(12) United States Patent
Niazi

(10) Patent No.: US 9,500,381 B2
(45) Date of Patent: Nov. 22, 2016

(54) MULTIUSE REACTORS AND RELATED METHODS

(75) Inventor: Sarfaraz K. Niazi, Deerfield, IL (US)

(73) Assignee: Therapeutic Proteins International, LLC, Chicago, IL (US)

( * ) Notice: Subject to any disclaimer, the term of this patent is extended or adjusted under 35 U.S.C. 154(b) by 244 days.

(21) Appl. No.: 13/225,407

(22) Filed: Sep. 3, 2011

(65) Prior Publication Data

US 2012/0231504 A1    Sep. 13, 2012

(51) Int. Cl.
| | |
|---|---|
| C12M 1/00 | (2006.01) |
| F24F 7/06 | (2006.01) |
| C12M 1/12 | (2006.01) |
| C12M 3/06 | (2006.01) |
| C12M 1/34 | (2006.01) |
| C12Q 3/00 | (2006.01) |

(52) U.S. Cl.
CPC ............. *F24F 7/06* (2013.01); *C12M 23/14* (2013.01); *C12M 25/14* (2013.01); *C12M 27/16* (2013.01); *C12M 29/06* (2013.01); *C12M 41/32* (2013.01); *C12M 47/10* (2013.01); *C12Q 3/00* (2013.01); *Y10T 137/0318* (2015.04)

(58) Field of Classification Search
CPC .................................................... C12M 23/26
USPC .................. 422/125, 513, 79; 210/178, 179; 435/289.1
See application file for complete search history.

(56) References Cited

U.S. PATENT DOCUMENTS

| | | | | |
|---|---|---|---|---|
| 5,459,069 | A | * | 10/1995 | Palsson ............. C07K 14/5403 435/289.1 |
| 5,997,814 | A | * | 12/1999 | Minerovic et al. ............. 422/29 |
| 6,544,788 | B2 | | 4/2003 | Singh |
| 7,141,154 | B2 | | 11/2006 | Lin et al. |
| 7,306,934 | B2 | | 12/2007 | Arora et al. |
| 7,799,548 | B2 | | 9/2010 | Arora et al. |
| 2005/0272146 | A1 | * | 12/2005 | Hodge et al. ............. 435/289.1 |

FOREIGN PATENT DOCUMENTS

WO        00/66706        11/2000

OTHER PUBLICATIONS

Ahmad et al., "Green Biofactories: Recombinant Protein Production in Plants;".Recent Patents on Biotechnology; 4: (3):242-59 (2010).
Atkinson, "Research studies predict strong growth for MBR markets;" Membrane Technology, pp. 8-10 (2006).
Bazinet, "Electrodialytic Phenomena and Their Applications in the Dairy Industry: A Review;" Critical Review in Food Science and Nutrition; 45(4):307-26 (2005).

(Continued)

*Primary Examiner* — Natalia Levkovich
(74) *Attorney, Agent, or Firm* — Therapeutic Proteins International, LLC; Sarfaraz K. Niazi

(57) ABSTRACT

A septum is positioned within a disposable vessel and defines a lower chamber and an upper chamber. The septum includes a plurality of apertures that provide fluid communication between the upper chamber and lower chamber. Compressed gas is introduced in the lower chamber to produce fine bubbles rising up throughout the vessel to produce a mixing and gasification needed for the growth of a biological culture and manufacture of a biological product in a nutrient medium. Adding a binding resin to the upper chamber allows harvesting, separation and purification of biological products in the reactor as a single unit operation.

7 Claims, 3 Drawing Sheets

(56) References Cited

OTHER PUBLICATIONS

Cui et al., "The use of gas bubbling to enhance membrane process," J. Membrane Science; 221:1-35 (2003).
Drews et al., "Potential and Drawbacks of Microbiology-Membrane Interaction in Membrane Bioreactors," Environmental Progress 24(4):426-433 (2005).
Ghosh et al., "Developments in liquid membrane separation of beta-lactam antibiotics," Bioseparaton, 6(2):91-105 (1996).
Hubbuch et al., "Biochemical engineering aspects of expanded bed adsorption," Adv. Biochem Engin/Biotechnol, 92:101-123 (2005).
Kraume et al., "Nutrients removal in MBRs for municipal wastewater treatment," Water Science and Technology. 51:391-402 (2005).
Le-Clech et al., "Fouling in membrane bioreactors used for wastewater treatment," Journal of Membrane Science 284:17-53 (2006).
Shirgaonkar et al., "Acoustic cell filter: a proven cell retention technology for perfusion of animal cell cultures," Biotechnology Advances, 22:433-444 (2004).
Shukla et al., "Recent advances in large-scale production of monoclonal antibodies and related proteins," Trends in Biotechnology, 28(5):253-61 (2010).
Singh et al., Solubilization and Refolding of Bacterial Inclusion Body Proteins, J. Biosciences and Bioengineering, 99(4):303-310 (2005).
Toda, "Theoretical and methodological studies of continuous microbial bioreactors," J. Gen. Appl. Microbiol., 49:219-233 (2003).
Voisard et al., "Potential of Cell Retention Techniques for Large-Scale High-Density Perfusion Culture of Suspended Mammalian Cells," Biotechnology and Bioengineering, 82(7):751-65 (2003).
Wu et al., "Preparation and application of organic-silica hybrid monolithic capillary columns," Electrophoresis, 32 (1):105-15 2011.
Pierce et al., "Scalability of a Disposable Bioreactor from 25L-500L Run in Perfusion Mode with a CHO-Based Cell Line: A Tech Review" Bioprocessing Journal, 3:51-56 (2004).
Ling et al., "Improvement of Monoclonal Antibody Production in Hybridoma Cells by Dimethyl Sulfoxide," Biotechnol. Prog. 19:158-162 (2003).
Weber et al., "Optimisation of protein expression and establishment of the Wave Bioreactor for Baculovirus/insect cell culture," Cytotechnology 38:77-85 (2002).
Singh, "Disposable bioreactor for cell culture using wave-induced agitation," Cytotechnology 30:149-158 (1999).

* cited by examiner

MULTIUSE REACTORS AND RELATED METHODS

BACKGROUND OF THE INVENTION

Reactors are used for a variety of physical, chemical and biological processing methods. Most reactors, including bioreactors, are complex mechanical devices that provide mainly the mixing and gasification of liquids to produce a variety of products. Bioreactors constitute a special type of reactors that are used to manufacture a variety of biological products ranging from wine to insulin (fermenters are a special type of bioreactors used for anaerobic reactions, even though the term fermenter is widely used to refer to bioreactors in general). The manufacturing of biological products involves several additional unit processes besides the process of growing the biological entities, all of which are tedious, expensive and cumbersome and completed outside the bioreactors, making the cost of manufacturing of biological drugs very high. The current methods of mixing and gasification used in bioreactors are also non-conducive to optimal production of biological products, further increasing their cost of manufacturing. There is a great unmet need for creating a reactor system that will be capable of producing biological products under the most optimal conditions, be able to combine all steps of biological product manufacturing within the same container and be of the lowest cost to own and operate. Such an invention will change the course of drug discovery and manufacturing, making it possible to provide life-saving new drugs to mankind at an affordable cost. Independently, the invention will serve many other industries where the it can be used for such specific purposes as mixing, gasification and sterilizing and holding solutions.

Liquid mixing is a major unit process in many industries including bioprocessing, chemical, and pharmaceutical manufacturing. The common methods of mixing a liquid (or a mixture of liquids and solids) in a container include use of an impeller, rocking or shaking the container, sparging gases to move liquid, ultrasonic waves and several combinations of these methods. Whereas, many of these mixing systems provide adequate quality of mixing as desired by the process, mixing of liquid in large containers, particularly the flexible disposable containers, remains a major problem. There is an unmet need to devise systems that will consume the least amount of energy, produce the lowest stress on the contents mixed, achieve mixing in the shortest period of time and produce consistent mixing results. Since mixing is a often an ancillary step in many other processes such a bioreaction, chemical reaction and manufacture of products, an efficient mixing system will yield highly profitable and time-saving operations in many industries. Whereas the term "liquid" is used in the present invention a fluid material, it refers to a nutrient medium or a culture medium or to a mixture of nutrient or culture medium and a biological culture interchangeably.

A variety of containers and methods have been developed over the years to carry out the mixing in the fermentation of microorganisms, particularly bacteria and yeast, on a commercial scale. Mixing in bioreactors serves many functions including diluting the metabolites, expel the gases produced and providing uniform gasification. The fermentation processes are generally conducted in stainless steel fermentation containers of several hundreds of thousands liters, with the fermentation methods including batch, fed-batch, continuous or semi-continuous perfusion. The cells within these containers are desirably kept in suspension, typically by rotating stirring blades located within the container, with gas exchange facilitated by the injection of air, oxygen or carbon dioxide into the container.

Gasification is a process of adding a specific gas to a nutrient medium; more commonly this includes adding gases like oxygen to grow biological organisms and tissues or using an inert gas to remove other gases like oxygen. A large number of applications from sewage treatment to bioprocessing of therapeutic proteins to operation of aquariums are dependent on gasification of liquids. In most hard-walled containers, gases are introduced by a sparger, a device with plurality of pores that diffuse gases inside a nutrient medium. A large variety of spargers are used, from the slow bubbling fish aquarium type to high-speed single point nozzles for the aeration of bioreactors. The efficiency of sparger is measured in the KLA value or liquid-gas transport coefficient that describes how fast a gas saturation is reached. It is expressed as liters per hour of gas that is absorbed in a liquid. For example, at room temperature (25° C.) the solubility of oxygen in water is about 8%; this decreases to about 6.5% at 37° C., the temperature most often used for bioprocessing. How fast is this maximum concentration of oxygen is reached in water upon starting gasification is a function of rate of gasification and mixing; also critical is the size of the bubble and thus the surface area of gas exposed to water. It is almost impossible to predict the KLA values since so many factors impact this value. However, higher efficiency systems of gasification allow for very high values of KLA, from 100-5000.

The above two processes form the critical requirement for a bioreactor design since the primary function is to provide sufficient gasification while mixing a nutrient medium in the presence of a biological culture. The current methods of fermentation have several drawbacks to their design. One is the introduction of shearing forces through the stirring blades and the cavitation of miniscule gas bubbles, both being detrimental to more sensitive cell types or organisms. Also, these containers should be rigorously cleaned between production runs to prevent cross-contamination, the latter being time consuming and requiring validation for individual cultures. Furthermore, the cost of stirred fermentors is relatively high on a volume basis, and thus these fermentors are commonly used over long periods of time. This, however, increases the risk of undesirable infection of mechanical failures. Perhaps most significantly, the optimization of culture conditions for stirred fermentors in a small scale cannot be transferred in a linear way to commercial scale production. For example, the fluid dynamics, aeration, foaming and cell growth properties change when the scale increases. In addition, for more delicate cell types or organisms, a large scale stirred fermentation container is not a viable device, even when more subtle stirring techniques such as airlift fermentors are used.

These drawbacks have led to the development of disposable fermentors. Examples of such disposable fermentors are systems based on wave agitation. See, e.g., U.S. Pat. No. 6,544,788; PCT Publication WO 00/66706. This type of fermentor may be used to culture relatively sensitive cells such as CHO cells (e.g., Pierce, *Bioprocessing J.* 3: 51-56 (2004)), hybridoma cells (e.g., Ling et al., *Biotech. Prog.*, 19: 158-162 (2003)), insect cells (e.g., Weber et al., *Cytotech.* 38: 77-85 (2002)) and anchorage-dependent cells (e.g., Singh, *Cytotech.* 30: 149-158 (1999)) in a single disposable container. Such disposable units are relatively cheap, decrease the risk of infection because of their single use and require no internal stirring parts as the rocking platform upon which these containers reside during use induces wave-like forms in the internal nutrient medium which facilitates gas exchange. However, this principle cannot be expanded to the size of hundreds of thousands of liters (such as the industrial fermentors) but are currently available from 1 liter to 500 liters (total volume of the disposable bag, available from Wave Biotechnology AG, Switzerland; Wave Biotech Inc., USA). Moreover, the hydrodynamics for each size of disposable bag will differ as a result of differences in depth and height. Therefore, the use of these disposable bags requires optimization and re-validation of each step in an up-scaling process.

Nutrient medium mixing is a major unit process in many industries including bioprocessing, chemical, and pharmaceutical manufacturing. The common methods of mixing a nutrient medium (or a mixture of liquids and solids) in a container include use of an impeller, rocking or shaking the container, sparging gases to move liquid, ultrasonic waves and several combinations of these methods. Whereas, many of these mixing systems provide adequate quality of mixing as desired by the process, mixing of nutrient medium in large containers, particularly the flexible disposable containers, remains a major problem. There is an unmet need to devise systems that will consume least amount of energy, produce lowest on the contents mixed, achieve mixing in the shortest period of time and produce consistent mixing results. Since mixing is a often an ancillary step in many other processes such a bioreaction, chemical reaction and manufacture of products, an efficient mixing system will yield highly profitable and time-saving operations in many industries.

There remains an unmet need to develop a sparging system that will allow a uniform and quick dispersion of gases throughout the liquid, reducing dependence on mixing to achieve a uniform concentration. This is of greater use in the deployment of bioreactors.

While the bioreactors are exclusively used for the purpose of growing bacteria or other cells, their role can be expanded to include other processes that can be completed within the bioreactor. There is an unmet need to develop a bioreactor for expressing and separating a biological product from other components in the culture medium, combining the steps of expressing and separating within the bioreactor by binding the biological product with a resin within a bioreactor, discarding the nutrient medium and eluting the biological product as a concentrated solution; this will eliminate at least two steps in the separation and purification of biological products—filtration or centrifugation to remove cell culture and ultrafiltration for volume reduction—and possibly three steps, including loading of biological products on the purification columns. For products which are expressed as inclusion bodies, the present will involve lysing the cells, solubilizing the inclusion bodies, folding the protein prior to binding it to a resin, all within the bioreactor.

A combination bioreactor will be more appropriately called a preparative bioreactor and this will significantly reduce the process time and cost while enhancing the yield by reducing the degradation of biological products during manufacturing. No such invention exists in the prior art of bioreactors.

Downstream processing involves steps for cleaning up crude biological products to yield high purity products. Traditionally, these steps involve using chromatography columns packed with highly specialized resins to capture and purify the desired biological products by the process of elution. With an exponential rise in the number of biological products being developed and marketed, there have been remarkable developments in the field of downstream processing; these have however not caught up with the developments in the upstream processing. A few years ago, an yield of 0.25 G of biological product per liter expressed by CHO cells was considered very high; today, we are hovering yields around 10 G/L making it possible to accumulate a very large quantity of biological products, particularly as the sizes of bioreactors have increased to thousands of liters. There are three steps that connect the upstream and downstream processing. First, the culture media must be filtered using fine filters (e.g., 0.22 microns) to remove cells (CHO cells have average size of 5 microns). This step utilizes an array of filters since the cells are likely to choke the filter surface easily and also require installing containers that will receive the filtrate. This requires containers of thousands of liters of capacity to match the size of the bioreactors. The next step is the reduction of the volume of filtrate since it is not possible to load such large volumes on columns that have limited flow rate. This is the stage where most often a cross-flow type filtration is used, again with a large bank of filters to complete the concentration process as quickly as possible. The mechanism of cross flow filtration place severe pressure on the solution and causes breakdown and precipitation of biological products resulting in losses of generally 10-20% at this stage. Both of these processes take a very long time and during this processing it is not possible to keep the biological product solution at a lower temperature resulting in the degradation of biological product as well. The third step is to load the concentrated solution in a chromatography column containing a binding media, a specific resin with affinity for the target biological product. Even though the volume of nutrient medium has been reduced considerably at this stage, the loading steps, nevertheless, takes substantial time to complete the loading.

The time and cost-consuming steps of filtration, chromatography and purification slow down the manufacturing process and add substantial capital cost requirement to establish cGMP-grade manufacturing operations.

Bioreactors used in the upstream processing are generally containers that allow growth of cell culture to express biological products and for reasons historic and traditional, a clear demarcation line exists between the expression of biological product and its purification. For this reason, no innovations have been made to add additional functions to the design of bioreactors while they do provide a large investment in a container that could possibly have multiple uses.

There is a large unmet need to stream line the entire process of biological manufacturing of products where the cost of manufacturing can be reduced substantially but combining several traditional steps in a single container, the bioreactor. Although bioreactor systems and related processes are known, improvements to such systems and processes will be useful in the preparation of a variety of products produced from a biological source at a substantially reduced cost, time and labor.

BRIEF SUMMARY OF THE INVENTION

The invention provides in one aspect a bioreactor suitable for use in preparing a variety of biological products. The bioreactor is suitable for housing a predetermined volume of nutrient medium and comprises: (a) a container having at least one interior wall; (b) a septum positioned within the container and defining a lower chamber and an upper chamber; (c) the septum having a plurality of pores that provides fluid communication between the lower chamber and the upper chamber; (d) at least one nutrient medium inlet; (c) at least one nutrient medium outlet; (d) at least one gas inlet; (e) at least one gas outlet.

A related aspect of the invention provides a method for producing a biological product from a nutrient medium of a predetermined volume comprising (a) providing a bioreactor in accordance with the aforementioned aspect of the invention; (b) introducing nutrient medium and a biological culture into the container; (c) passing the gas through the septum and into the nutrient medium; (d) detecting the density of cells in the nutrient medium and the concentration of the biological product expressed at predetermined time intervals; (e) adding to the bioreactor a resin in the lower chamber and allowing the drug product to bind with the resin; (f) draining out the nutrient medium and the biological culture from the container when the density of the cells and the concentration of expressed biological material in the nutrient medium in the container reaches a predetermined low value; (g) washing the resin with water or buffers as necessary, draining the washings; (h) removing the resin-drug bound complex and loading it onto a purification column or treating the resin-drug bound complex with a buffer to disassociate the drug from the resin-drug complex and collect a concentrated solution of the expressed drug for further purification. Additionally, the washing steps with buffers are modified to provide the purification function as well.

Besides the specific use of the invention for the production and purification of biological products, it can be generally used to prepare solutions like the nutrient medium, buffers, drug solutions, etc., and also to serves as a sterilizing container and as a pressurized transfer container in a variety of pharmaceutical manufacturing operations. And finally, the container described in the present invention will be capable of performing the downstream function as well, consolidating all functions of biological product manufacturing into one container.

DETAILED DESCRIPTION OF THE INVENTION

In one aspect, the present invention provides a bioreactor suitable for preparing a biological product from a predetermined volume of nutrient medium, and a related method of use.

Figure 1:
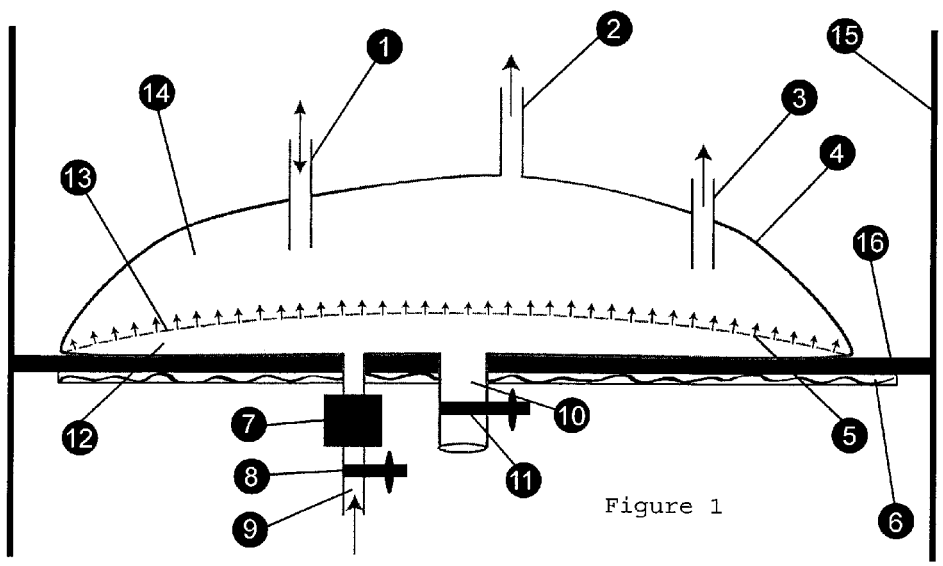
FIG. 1 is a side sectional view of a bioreactor in accordance with a preferred embodiment of the invention.

Turning initially to FIG. 1, a side sectional view of a preferred embodiment of the inventive bioreactor is illustrated. In this embodiment, there is provided a container 4 having at least one interior wall and, optionally, a support 16 for the container 4 affixed on a vertical structure 15.

The container 4 provides a receptacle in which the nutrient medium resides, and in which growth of the desired product occurs. The container has septum 13 positioned within the container and defining a lower chamber 12 and an upper chamber 14, the septum having a plurality of pores 5 that provides fluid communication between the lower chamber and the upper chamber. The container 4 comprises several ports including a gas inlet 9, which comprises a sterilizing filter 7 and a valve 8. The gas inlet 9 is connected to a source of compressed gas 19. Once the gas source is turned on, gas enters the lower chamber 12 through the gas inlet 9 and after passing through the sterilizing filter 7. Since the plurality of the pores 5 in the septum 13 have a small diameter, the flow of gas across the septum 13 is impeded, resulting in a build-up of pressure inside the lower chamber 12. Once a critical pressure is reached in the lower chamber, the gas breaks through the plurality of pores 5 and into the upper chamber 14 and traverses through the contents of the container 4, breaking the surface of the liquid in the container and finally exiting the container through a gas outlet 2. The container also includes a liquid outlet port 10 and a valve 11 that controls removal of the nutrient medium and biological culture. The upper chamber further comprises a liquid inlet port 1 to introduce nutrient medium and biological culture to the container 4 and optionally a sampling port 3 to remove the nutrient medium periodically for analysis of its contents.

Returning to FIG. 1, it is desirable that the container 4, particularly a flexible container as further described herein, be supported by a support, the latter preferably comprising platform 16 and side walls 15. The platform and side walls may be comprised of any suitable material, e.g., metal or rigid polymers, so long as it is sufficiently rigid to support the flexible container. Desirably, and as illustrated in FIG. 1, the platform (and the container) is raised relative to the floor or other surface. This permits inlets and outlets to be located on the side or the container which rests on the platform. For example, and as illustrated in this embodiment, it is desirable that the at least one gas inlet 9 of the container 4 be located on a portion of the container which is coextensive with the platform, wherein the platform includes an opening therethrough which permits the gas to pass through the platform and into the container 4 through the gas inlet 9. The container 4 rests on a support surface 16, which is in turn supported by a vertical structure 15, if needed. The lower surface of the support surface 16 additionally includes a means of heating of cooling 6 for the container 4.

The gas inlet 9 has an additional control valve 8 that is placed between the container 4 and the sterilizing filter 7; the control valve 8 is between the source of compressed gas and the sterilizing filter 7.

The hard support platform 16 additionally contains a heating element 6 attached to the side opposite to that that is in contact with container 4 to allow the nutrient medium to be kept at a desired temperature, most likely at 37° C.

Figure 2:
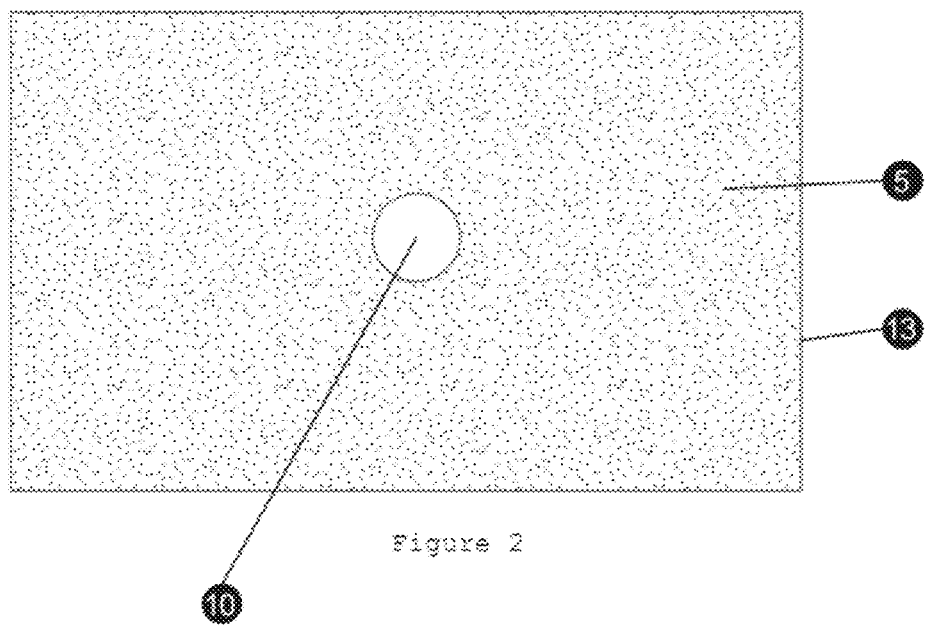
FIG. 2 is a topical view of the septum in a bioreactor in accordance with a preferred embodiment of the invention.
Figure 3:
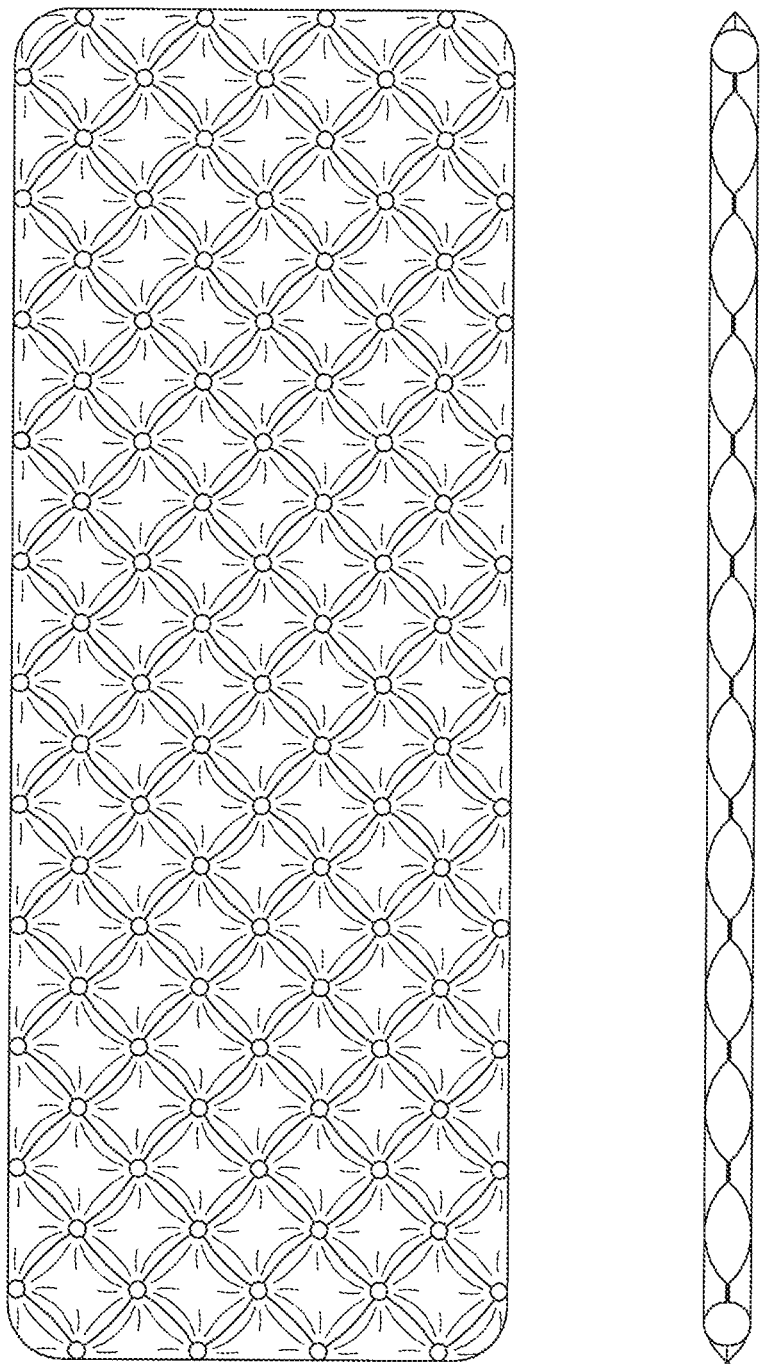
FIG. 3 is a side sectional view of the bioreactor illustrating a tufted septum.

FIG. 2 shows a topical view of the septum 13, wherein the plurality of holes 5 is distributed evenly or in specific patterns throughout the horizontal surface of the septum 13. More specifically, the septum 13 comprises a flexible sheet of plastic of approximately the same size as the bottom dimension of the container 4 and that it has been perforated by mechanical means such as a laser gun, to create pores proportionally placed throughout the surface. The septum is sandwiched between the top and the bottom layer of the flexible bag. Optionally, the septum can be attached to the bottom surface of the bag by tufting it to the bottom surface using heat treatment, thus preventing bloating of the septum 13. The pressure in the lower chamber of the forces the gas out of the pores 5 as fine bubbles inside the nutrient medium; it is understood that the nutrient medium will be present in both chambers of the container 4.

Aspects of the present invention address various deficiencies in known bioreactor designs including, for example, maintaining a desirable level of suspension of the culture in the medium, and assuring proper aeration, each of which supports growth of the culture. Known bioreactors utilize a variety of means to provide adequate suspension and aeration including the use of impellers and/or movement of the container to effect mechanical circulation. In the inventive bioreactors, however, the interior and exterior of the container is free of mechanical agitation devices, such as impellers and the like, and the nutrient medium therein need not be moved via any mechanical means during operation of the bioreactor. Moreover, there is no need to shake or otherwise move the container during operation of the bioreactor; the bioreactor may remain stationary during operation.

The inventive bioreactor includes a septum as a flexible sheet that acts as a sparging filter, comprising a plurality of pores along its entire surface, which permit the gas to be emitted vertically from the septum into nutrient medium. In this septum, the mean diameter of each of the plurality of pores does not exceed about 50 μm, desirably from about 1 μm to about 50 μm, more desirably from about 1 μm to about 20 μm, and most desirably from about 1 μm to about 10 μm, wherein gas bubbles in the aqueous nutrient medium do not exceed about 500 μm in diameter. Gas bubbles having a mean diameter of about 1000 μm or greater were found to exert damaging effects on certain culture media. Preferably, the mean pore diameter does not exceed about 10 μm, with the gas bubble size not exceeding about 100 μm.

When in use, the septum is in such orientation within the container that the plurality of pores therein are fully immersed in the nutrient medium, and the gas passes through and is emitted from the septum to provide a substantially uniform distribution of the emitted gas throughout the nutrient medium. Thus, the bioreactor is designed to promote maximum gas transfer into the nutrient medium, with minimal movement of the culture, yet enough to maintain the culture in suspension. The use of a septum which provides relatively small diameter gas bubbles was found to provide sufficient gas transfer over a relatively long distance without producing significant damaging turbulence.

The intensity of the flow of gas from the lower chamber to the upper chamber is inversely proportional to the size of pores in the septum; thus, if a gentler mixing is required, the septum will have larger size pores.

The absorption of gas into liquid is represented by a constant, KLA with units as liters per hour, for instance. The absorption of gas into liquid is a function of two parameters, the mixing of liquid and the flow of gas into liquid; when gas is present at smaller size bubbles, the surface area of bubbles per unit of the quantity of gas is large and thus results in a faster absorption. Generally, a KLA value of 100 or higher will be required to grow bacteria while a much smaller value will provide adequate for growing cells like the Chinese Hamster Ovary cells. The invented bioreactor is capable of achieving KLA values to 1000 or more making it most appropriate for growing all types of cells and organisms. Such high value of KLA had never been possible and thus the prior art does not suggest the utilization of disposable plastic bags for growing bacteria or other such organisms and cells that require a large KLA value.

While the container may be of any suitable shape, e.g., rectangular, cuboid or cylindrical, it is desirably generally rectangular, wherein a central axis of the container is collinear with the axis of the horizontal septum. As the pores of the septum are distributed along its surface, and it is disposed within the container so as to provide full immersion of all pores within the nutrient medium, the septum surface is able to emit a constant stream of relatively small bubbles from the base of the container towards the top surface of the container. This arrangement was found to assist in reducing undesirable shear forces, and to increase yield, relative to known bioreactors. It is believed that, when the gas flow into the septum is optimized, a laminar shear is induced which is sufficient to move any metabolic products away from the culture cells without disturbing any clusters of such cells, thus maintaining optimal production of such products. This arrangement, which provides for relatively uniform gasification of the nutrient medium, also has the benefit of minimizing stratification of the nutrient medium typically seen in bioreactors wherein aeration is provided only at a focal point in the bioreactor, wherein overcrowding results in non-homogenous productivity.

As the relatively fine bubbles move upward in the container, the bubbles tend to coalesce and become relatively less effective in gas transfer. Thus, there is a relationship between the rate of gas emission into the nutrient medium and the size of the container. It is noteworthy that as gas pressure builds in the lower chamber at the base of the container, it is expected to be the highest at the point of gas inlet and reduce at a distance away from the gas inlet. While many methods are available to provide a more uniform pressure, and thus more uniform outflow of gas through the septum, a more suitable method is to install gas inlets at frequent intervals. Depending on the geometry and the size of the container, the gas inlets are desirably installed at a distance no more than 2 feet apart, most preferably no more than 1 foot apart; however, the frequency of gas inlets is not critical to the performance of invention. The most significant inventive part is that the pressure of gas be such that it allows gas bubble to break through the entire surface of the septum and also through the surface of the nutrient medium.

The compressed gas feeding the septum may be oxygen, but also may be air; the inventive bioreactor is capable of using gas with exceptional results. Moreover, the container may comprise one or two gas inlets. In the latter case, the gas may be fed into both ends of the septum.

The septum desirably comprises a flat flexible membrane of thickness ranging from 4-10 mil; the membrane has a porous structure creating by inserting holes uniformly throughout the membrane as shown in FIG. 2. These holes can be made by any mechanical means or by cutting using a laser beam. In most instances, the pores are present at every 0.25 to 0.5 inches and have a diameter of 10-50 microns.

Gasification may be run continuously, periodically, or in some cases, in response to certain events, e.g., within a bioreactor system and/or within an individual container. For example, one or more sensors may monitor the amount of gasification, the degree of foaming, the amount or concentration of a substance in the container, and respond by initiating, reducing, or increasing the degree of gasification or one or more compositions of gases.

As previously mentioned, the container desirably may include one or more sensors or probes for monitoring one or more process parameters inside the containers such as, for example, cell density, temperature, pressure, pH, dissolved oxygen (DO), dissolved carbon dioxide ($DCO_2$), mixing rate, and gas flow rate. The sensors for DO, pH and $DCO_2$ are desirably optical sensors, with the first two more desirably being disposable (e.g., TruFluor sensors, Finesse Solutions LLC, Santa Clara, Calif. or CellPhase sensors, Fluorometrix Corporation, Stow, Mass. 01775). Each sensor is intended to be in communication with a computer-implemented control system (e.g., a computer) for calculation and control of various parameters and for display and user interface. Such a control system may also include a combination of electronic, mechanical, and/or pneumatic systems to control the aforementioned processing parameters as required to stabilize or control the parameters (e.g., pH may be adjusted by the addition of $CO_2$ or ammonia). It should be appreciated that the control system may perform other functions and the invention is not limited to having any particular function or set of functions.

The one or more control systems described herein can be implemented in numerous ways, such as with dedicated hardware and/or firmware, using a processor that is programmed using microcode or software to perform the functions recited above or any suitable combination of the foregoing.

The processing device may also be in communication with various devices which can adjust the process parameters toward predetermined acceptable levels, for example, activating a heater, activating a gas inlet valve to adjust the oxygen or $CO_2$ levels, activating the gas outlet valve to reduce gas pressure in the headspace, and the like.

Advantageously, the bioreactor may further include a controllable heating element 6, desirably located between the upper surface of the platform and the lower portion of the container. This element, when activated, is able to increase the temperature of the nutrient medium with the container to a level which is optimal for the particular nutrient medium therein. The heating element may comprise a heat exchanger, a closed loop water jacket, an electric heating blanket, or a Peltier heater. Other heaters for heating a nutrient medium inside a container are known to those of ordinary skill in the art and may be used alone or in combination with the foregoing device. The heater may also include a sensor for detecting the temperature of the nutrient medium inside the container, e.g., a thermocouple and/or a resistance temperature detector (RTD). The thermocouple may be operatively connected to a process control module to control temperature of the contents in the container. Optionally, a heat-conducting material may be embedded in the surface of the container to provide a heat transfer surface to overcome the insulating effect of the material used to form other portions of the container.

Optionally, cooling of the container may be provided by a closed loop water jacket cooling system, a cooling system mounted on the platform, or by standard heat exchange through a cover/jacket associated with the support, for example, a heat blanket or a packaged dual unit which provides heating and cooling may a component of a device configured for both heating/cooling but may also be separate from a cooling jacket. Cooling may also be provided by Peltier coolers.

In a related aspect, the bioreactor may be operated to provide for perfusion. In perfusion, the biological cultures are placed into steady-state operation, thereby permitting operation of the bioreactor to be extended for weeks, and perhaps months. The perfusion bioreactor of the invention may be used to produce secreted products, produce large amounts of slow growing cells, or function as an artificial organ such as an extracorporeal liver. The design make this device ideal for hospital use in cell and gene therapy applications.

During perfusion, a nutrient medium (the product, or byproducts) is removed from the bioreactor, while nutrients are introduced into the container periodically during operation, typically at a relatively slow rate, in order to maintain the volume of nutrient medium therein reasonably constant. In the case of secreted products, this nutrient medium desirably contains a product that requires purification. When the desired product is the culture itself, nutrient medium containing toxic byproducts is removed during operation.

Generally, one desires to prevent cultures from leaving the container during removal of the nutrient medium therefrom; the present invention provides for this, as further described herein. In practice, a relatively small amount of cell loss (<10%) is tolerated in order to remove dead and dying cells and to promote a low level of regrowth.

One means for controlling the volume of culture (liquid) in the container is by controlling the weight of the container, or the entire bioreactor assembly, so that the weight remains constant. Desirably, a scale which determines the weight of the bioreactor provides feedback to a valve control which adjusts the valves associated with the container inlet and outlet to maintain the desired weight, and thus nutrient medium volume in the container.

During operation, the container is at least partially filled with nutrient media and biological cultures. Oxygen, necessary for biological culture metabolism, is provided by gas introduced into the container via the septum 13. Exhaust gas is vented from the chamber through the gas outlet 2. The container is also provided with a culture/nutrient media inlet and outlet 1 as well as a sampling port 3.

In one aspect, the present invention achieves two distinct functions of traditional bioreactors by using one device, the septum, which provides gas dispersion as well as the mixing of the contents of the bioreactor; the latter function is needed to dilute the metabolites of fermentation as well as force the exhausting of any soluble gas forms like carbon dioxide formed in the fermentation processes using bacteria. Thus in one aspect, the present invention acts like a bubble reactor, even though it deviates significantly from the classical bubble reactors.

Gaseous bubbles have often been used in various industrial operations; for example, slug bubble bioreactors produce a large bubble that rises from the bottom of a container, pushing the culture media upwards as the bubble moves up and is discharged at the surface. Sparger of several types are installed at different locations inside a container to force gas or other gases to force the movement of nutrient medium inside the container. The U.S. Pat. No. 6,237,898 describe a bubble elevator that includes an orifice intermediate between the gas tapping point for entraining nutrient medium and the top opening for ejecting the air/nutrient medium mixture. The U.S. Pat. No. 7,600,741 describes a gas bubble generator suitable for use in anaerobic digestion systems for treating waste sludge. The gas bubble generator is submerged within a large body of nutrient medium and is attached to a stack pipe. The U.S. Pat. No. 7,374,675 describes a system and method of aerobic wastewater treatment that provides large mixing bubbles along with small oxygenating bubbles supplied by diffusers. The mixing bubbles are large enough to move wastewater and generate a mixing current as they rise to the surface.

The above represent just a few examples of how various devices including spargers and diffusers are used for the aeration of liquids using bubbles while also making it possible to mix the liquids in a container. While many of these systems are suitable for smaller operations, mixing becomes a serious challenge in larger containers where pockets of unmixed liquids may accumulate, particularly in containers that are horizontally laid out like the flexible bags. Generally, a solution is found in increasing the gasification rate and intensity of mixing that whips up the liquids, requires very high energy, often causes degradation of the product and in those cases where a biological organism or cell is involved, results in reduced productivity.

The unmet need of a universal mixing system is addressed in the present invention wherein a gas dispersion system is installed at the bottom of a mixing container such that the entire bottom of the container acts as a sparger; this allows nutrient medium to move upwards throughout the container providing adequate mixing. To achieve this goal, several design parameters become crucial. For example, it is necessary that the gas be pushed as fine bubbles throughout the bottom surface and rising vertically to the top of the nutrient medium surface. The intent is to keep the fluid movement as most conducive optimal mixing. The size of gas bubbles and the requirement that they break the top surface of the nutrient medium at all points is important. One way to achieve this is to provide a septum with pores creating fine bubbles throughout the bottom surface of the container allowing these bubbles to rise upward to force a desired mixing profile. The septum can be made of various materials like ceramic, plastic, metal or any other such hard material. As gas will escape through the septum pores forming an upward stream that pushes the nutrient medium up and stir the nutrient medium as bubbles move up, coalescing and forming larger bubbles and thus creating a turbulent mixing. As bubble size increases, it causes the nutrient medium to be pushed around resulting in the interruption of the laminar flow and the Reynold number increases to provide a turbulent mixing. Another critical design feature is that the pores are of same size throughout the surface of the septum creating an imbalance of gas flow, with higher flow rates nearer to the source of gas input (because of higher pressure), moving the nutrient medium more rapidly in the inside core if the source of gas is in the center) compared to other parts of the container where the flow rate is lower because the pores are farther away from the source of gas introduced and thus push smaller volume of gas. This creates a differential movement of nutrient medium in various parts of the container creating a cascade effect that can further enhance the mixing. It is important to realize that a critical component of this invention is to provide sufficient gas flow so that gas bubbles break the top surface of the nutrient medium at all point.

The gas inlet is placed preferably as central to the horizontal surface of the container to provide a uniform distribution of gas pressure behind the septum. In those instances where the surface area is large such in large reactors, it may be necessary to introduce gas at various points along the horizontal axis to avoid larger pressure drops across the horizontal axis. In the absence of this modification, the pressure of gas used will have to be made very high to make sure that gas breaks the surface of the liquid.

The pores in the septum layer or the septum need to be of a dimension such that the gas is not lost instantly as large bubbles to the container and for this purpose, the size of pores is best kept at below 50 micron range; the size of pores determines the flow rate and thus results in pressure drop; larger pore sizes will cause the gas to escape without forming a pattern of flow. The optimal pore size will depend to a great extent on the viscosity of the liquid, the height of gas travel and the volume of liquid, all those parameters that determine the breakthrough pressure needed to push the gas inside the container as well as cause it to break the top surface of the nutrient medium as well.

The bioreactor shown in FIG. 1 is operated by starting flow of gas that begins to flow out of the pores in the septum and moves upwards pushing the liquid. The flow rate of the gas is maintained such that the entire upper surface of the nutrient medium begins to show bubbles breaking through it as an indication that the entire nutrient medium is under motion assuring that there will be no dead volumes anywhere in the container.

The present invention thus addresses the critical mixing needs in a bioreactor while resolving the need for gasification. Historically, an impeller device is used that rotates fast inside a nutrient medium volume that creates a circular movement to mix liquids. Since the energy transfer to liquids is highly efficient, this remains as the most widely used method. The goal of impellers is to create a large enough circle of movement that will cause the movement of entire nutrient medium; in some designs larger size impellers achieve it or smaller size impellers achieve it by high velocity. A good example of this is found in the movement of boats. Large ships have impellers that move at a very slow speed but displace a very large volume of nutrient medium while the onboard motors on smaller boats have a very small fan that rotates at a very high speed. In nutrient medium mixing, often the containers have baffles to break the laminar movement of nutrient medium generated by the circular motion of the impeller to increase the mixing efficiency. In the bioprocessing industry, a bioreactor or a fermenter is a good example of a container that is in need of a good mixing system. For hard-walled containers used as bioreactors or fermenters, the obvious choice is to install impellers to generate movement of nutrient medium and these are operated at a very high speed, 400-500 rpm, most often to achieve the mixing efficiency required. However, it is widely known in the science and the art of growing biological organisms and cells that these grow better when allowed to stay in colonies or aggregates; the most frequently used method of mixing by using impellers destroys the aggregates and breaks the colonies resulting in a less than optimal growth yield. A more desirable solution will be to provide as laminar a mixing possible to reduce the shear on the living cells and organisms while assuring homogeneity of the nutrient medium throughout its volume. This can be readily achieved as taught in the present invention. First, a septum is chosen such that when placed at the bottom of the container, it covers the entire base of the container. This filter can be a disc-shaped ceramic device or a stainless steel device that has pores on both sides or only on one side (if the filter has pores on both sides, these can be blocked on one side by coating the filter with a resin). There is a gas inlet attached to the filter such that the inlet is as central to the filter as possible. For cylindrical containers, this will not be difficult but for all other shaped there will inevitably be a misbalance as the longer edge of a rectangular shape will be closer to the gasification inlet than the shorter edge. In all instances, the pressure of gas near to the gas entry point will be higher resulting in faster flow through the pores nearest to the inlet; to circumvent this, the density of pores near to the inlet point can be reduced, either by design (e.g., when creating a perforated septum or blocking some pores nearer to the gas inlet). This configuration is shown in FIG. 2. While this feature of variable density of pores is described as an element of invention, it is not required since the behavior of nutrient medium will depend to a great degree on several other factors which include nutrient medium density, viscosity, height of nutrient medium column, temperature of liquid, the volume of liquid, the dimensions of the container, the pressure and flow of gas, the type of septum used, etc., the factor of variable density of pores will impact but to an uncertain degree.

In some instances, having a uniform density of pores may be beneficial, as it will result in a stratification of the columns of liquids rising above with the center column having the fastest velocity. This will create a cascade effect, like a fountain with a major spout in the center, to produce efficient mixing.

The present invention produces both vertical and horizontal mixing; as the gas bubbles rise, they coalesce and produce a compression force of variable dimension producing lateral flow of liquid. The time taken to achieve a homogenous mixing will depend to a great degree on the density, viscosity, temperature, gas flow rate and the dimension and geometry of the container. All of these parameters can be readily validated by a single mixing validation study that will require adding a dye to the nutrient medium and studying its distribution and concentration over time; based on these data, each of the container types and the nutrient medium mixed in it routinely are validated.

For more specific applications, the two uses described above are combined in the present invention to provide optimal conditions for the growth of cells and organisms in culture media. This will then constitute a stationary bioreactor of the lowest cost and of the highest efficiency possible. Thousands of applications of these types of bioreactors are possible, from the wine industry to recombinant drug production. Some of these applications are described later in this application.

So far, the utility of the present invention was described in terms of its ability to perform two critical function in bioreactor function: gasification and mixing. These are routine function, though never combined together in a stationary bioreactor using a single source of energy. However, there remains many function that can be added to the functionality of the bioreactor such as harvesting and capturing of proteins. The present invention relates to a novel bioreactor design for expressing and separating a biological product from other components in a nutrient medium, which combines the steps of expressing and separating within the bioreactor by binding the biological product with a resin within a bioreactor, discarding the nutrient medium and eluting the biological product as a concentrated solution; this allows elimination at least two steps in the separation and purification of biological products—filtration or centrifugation to remove cell culture and ultrafiltration for volume reduction—and possibly three steps, including loading of biological products on the purification columns. A further application will include performing the purification step within the bioreactor container as demonstrated in the present invention.

For products which are expressed as inclusion bodies, the present invention allows cell lysis, inclusion body solubilization and protein refolding within the bioreactor.

The present invention significantly reduces the process time and cost while enhancing the yield by reducing degradation of biological products during manufacturing; additional benefits of the present invention include avoiding perfusion process and reducing toxicity of the expressed biological products to cell culture. No such invention exists in the prior art of bioreactors.

The time and cost-consuming steps of filtration, chromatography and purification slow down the manufacturing process and add substantial capital cost requirement to establish cGMP-grade manufacturing operations. The present invention offers the most desirable solution to these impediments in drug discovery and drug manufacturing fields.

There two major types of recombinant expressions of biological products, one is the soluble form of biological product that is secreted into nutrient medium by the cells as most often seen in the use of Chinese Hamster Ovary cells and the other is the retention of biological product inside the cell forming an inclusion body, as most often seen in the case of using E. Coli for expression. Recent advances in genetic engineering have been able to encode the genes of bacteria that will secrete soluble proteins instead of retain them inside as inclusion bodies. This is to avoid the cumbersome process of cell-lysis and inclusion body solubilization.

Historically, biological products expressed in nutrient medium are separated from the medium by first removing the biological culture by a process of centrifugation or filtration. This step is followed by reducing the volume of medium to about $\frac{1}{10}$ to $\frac{1}{20}$ to make it possible to load the nutrient medium within a reasonable time on purification columns. While these process steps have been widely validated and function very well, the practicality of using these steps becomes very difficult when large volumes of medium is handled. Today, it is not uncommon to see bioreactors processing thousands and even hundreds of thousands of liters of medium at a time. To accommodate this, companies use very large-scale filtration and volume reduction methods that cost millions of dollars to install and millions more to operate and maintain. There is a very large unmet need to simplify these processes, reduce the cost of production and make the technology accessible to thousands of researchers and smaller companies who cannot afford such large investments. Circumventing these process hurdles will also make it possible to produce drugs based on these biological drugs cheaper to manufacture and thus increase their affordability to billions of people around the world who are not able to afford these drugs.

The key to the present invention lies in following a contrarian teaching. While all manufacturers follow the path described above involving removal of components from a broth ready for purification, it will be prudent to examine the utility of first removing the target biological product instead and discarding what is not needed, instead of removing step by step what is not needed, as currently practiced.

The present invention capitalizes on the recent availability of many resins that are capable of binding biological products in large quantities. Most modern resins will bind between 20-125 mg of biological product per mL of resin. Many of these resins are highly specific to the biological products and many of them can be combined to remove any type and quantity of a biological product from a solution by a simple process of physicochemical binding that is strong enough to retain the biological products attached to the resin while the nutrient medium is removed from the bioreactor. The art has also advanced significantly in the field of biological product purification wherein we now have a much better ability to elute these bound biological products from resins by adjusting the pH, the ionic strength or other characteristics of the eluting buffer to break the binding between the resin and the biological product. This allows removal of biological products from a bioreactor as a highly concentrated solution that is ready for further purification and in some instances it can even be the final product for use.

Affinity chromatography is a separation technique based upon molecular conformation, which frequently utilizes application specific resins. These resins have ligands attached to their surfaces, which are specific for the compounds to be separated. Most frequently, these ligands function in a fashion similar to that of antibody-antigen interactions. This "lock and key" fit between the ligand and its target compound makes it highly specific.

Many membrane proteins are glycobiological products and can be purified by lectin affinity chromatography. Detergent-solubilized proteins can be allowed to bind to a chromatography resin that has been modified to have a covalently attached lectin.

Immunoaffinity chromatography resin employs the specific binding of an antibody to the target biological product to selectively purify the biological product. The procedure involves immobilizing an antibody to a column material, which then selectively binds the biological product, while everything else flows through.

Inclusion bodies upon solubilization exposes hydrophobic groups while there remain chemical groups on denatured proteins capable of binding to resin (Singh and Panda, 2005), allowed separation of these proteins during the stages of refolding to native state.

Some of the state of the art resins binding technologies include:
a. Novozymes's newly patented Dual Affinity Polypeptide technology platform replaces Protein A process steps with similar, but disposable, technology.
b. Stimuli responsive polymers enable complexation and manipulation of biological products and allow for control of polymer and biological product complex solubility, which results in the direct capture of the product without centrifuges or Protein A media, from Millipore Corp.
c. Mixed mode sorbents to replace traditional Protein A and ion exchange, for improved selectivity and capacity with shorter residence times. These media, with novel chemistries, include hydrophobic charge induction chromatography, such as MEP, and Q and S HyperCel from Pall Corp.
d. Monoliths, involving chromatography medium as a single-piece homogeneous column, such as Convective Interaction Media monolithic columns from BIA Separations.
e. Simulated moving beds, involving multicolumn countercurrent chromatography, such as BioSMB from Tarpon Biosystems.
f. Protein G (multiple vendors).
g. Single domain camel-derived (camelid) antibodies to IgG, such as CaptureSelect from BAC.
h. New inorganic ligands, including synthetic dyes, such as Mabsorbent A1P and A2P from Prometic Biosciences.
i. Expanded bed adsorption chromatography systems, such as the Rhobust platform from Upfront Chromatography.
j. Ultra-durable zirconia oxide-bound affinity ligand chromatography media from ZirChrom Separations.
k. Fc-receptor mimetic ligand from Tecnoge.
l. ADSEPT (ADvanced SEParation Technology) from Nysa Membrane Technologies.
m. Membrane affinity purification system from PurePharm Technologies.
n. Custom-designed peptidic ligands for affinity chromatography from Prometic Biosciences, Dyax, and others.
o. Protein A- and G-coated magnetic beads, such as from Invitrogen/Dynal.
p. New affinity purification methods based on expression of biological products or MAbs as fusion biological products with removable portion (tag) having affinity for chromatography media, such as histidine) tags licensed by Roche (Genentech).
q. Protein A alternatives in development, including reverse micelles (liposomes), liquid-nutrient medium extraction systems, crystallization, immobilized metal affinity chromatography, and novel membrane chromatography systems.
r. Plug-and-play solutions with disposable components (e.g., ReadyToProcess), process development ÄKTA with design of experiments capability, and multicolumn continuous capture, from GE Healthcare.

It is surprising that while great advances have been made in the design of resins available to capture biological products, these have been only used in the downstream processing of purification. Adding resins to a crude mixture of biological products and host cells will be no different than the current process that simply concentrates the same medium and loads it onto columns with all of the impurities in it. The only difference will be that when practiced at the end of the bioreaction cycle, this will require sufficient resin to bind almost the entire biological product. Aiming at a cell line that produces 1 mg/mL of protein and that the binding capacity of the resin used is 50 mg/mL, this will require 20 L of resin when operating a 1000 L bioreactor. The cost of resins suitable for the manufacturing of monoclonal antibodies can range from $15-$20,000 per liter, such as Protein A. As a result, most manufacturers would rather run several sub-batches of purification using a smaller quantity of the resin. However, given that these can be used for hundreds of times, the cost is readily amortized for use and avoids the tediousness and regulatory hurdles in preparing sub-batches.

While a larger quantity of resin is added at the end of process treatment, these additions are spread over time if the present invention is used where the classical perfusion method is replaced with resin capture. By adding various amounts of resin as the bioreaction proceeds, the expressed protein is removed from the nutrient medium. It is important not to add a larger quantity of resin than needed at any given time since it is inevitable that other components in the nutrient medium get lost to resin as well if the resin used has a non-specific binding characteristics. This would not be the case if an immune-affinity or specific structure resin such as Protein A is used. Where it is inevitable to lose nutrients to the resin, these should be replaced along with the addition of resin to the bioreactor. Some caution is necessary when using a resin to bind proteins during the process of bioreaction as these must be properly sterilized. It is for this reason, it may be advantageous to use a more specific binding resin that can be added during the sterilization of the container by gamma radiation.

Additionally, one embodiment of the invention may be practiced by using the least expensive resins to generically bind all soluble organic components and then elute them instantly using a buffer without any concern for the profile of elution to separate these components. Such generic resins are very inexpensive and may not even have to be reused.

The present invention thus offers a method of biological product harvesting and purification in the same bioreactor where the biological product is produced.

One of the main objectives of the present invention is to eliminate certain unit processes, which are cumbersome and expensive such as separation of biological culture at the end of the bioreaction cycle. Most bacteria are about 1μ in diameter and the Chinese Hamster Ovary cells about 5μ in diameter. The binding resin is separated from the nutrient culture by the septum 13 in FIG. 1. Since the porosity of the septum is below the size the resin, the resin introduced in the upper chamber through the liquid inlet 1, will stay inside that chamber. At the end of the bioprocess cycle, an appropriate quantity of resin is introduced in upper chamber and the container allowed to stand long enough with purging of gas to allow complete binding. Once the protein binds to resin completely as determined by testing the medium for reduction in the concentration of protein, the nutrient medium and biological culture are drained through outlet 10 by opening the stopcock 11. Once the nutrient medium is removed, the stopcock 11 is closed and water or buffer solutions introduced in the container 4 through inlet 1 to wash the resin to further remove any biological culture that may have been adsorbed onto the resin; the washings are then drained out through liquid outlet 10. the buffer may be used alternately to remove the binding of the drug from the resin and thus making a highly concentrated solution of the drug which can then be drained through port 10 by opening the stopcock 11. The end result of this operation will be complete harvesting, at the least, and a resin ready for loading into purification column, at the best. This unit operation will thus replace three separate unit processes: removal of cells by centrifugation, reduction of volume by ultrafiltration and loading of column. It is noteworthy that by performing all of these operations within the bag also eliminates the need to use additional containers. Another most significant advantage of the methods disclosed comes in increased production yields. It is well established that the process of centrifugation filtration, which are conducted under high pressure, inevitably decompose biological products. By avoiding the centrifugation and filtration steps, it is envisioned that the product yields will improve substantially.

The very nature of the recombinant product makes it unstable. The instability of a recombinant biological product can be either physical or chemical. Physical instability can be related to such things as denaturation of the secondary and tertiary structure of the biological product, adsorption of the biological product onto interfaces or excipients, and aggregation and precipitation of the biological product. Chemical instability of a biological product results in the formation of a new chemical entity by cleavage or by new bond formation. Examples of this type of instability will be deamidation, proteolysis and racemization. Any changes to the manufacturing process that reduce the cycle of production, exposure to harsh conditions such as high pressures across membranes in cross-flow and sterile filtration, etc., will increase the stability and the final yield of production. In one method of batch processing, the biological products are harvested at the end of the cycle that might be as long as several weeks of continuous expression; while many biological products will survive the 37° C. environment for that length of time, a few will degrade over period of time.

Another most useful application of the invention is in capturing the proteins throughout the period of expression. By capturing the biological products through formation of resin-biological product complex, the stability of and thus the yield of production can be increased since in the complex stage, the molecules are immobilized and thus less likely to degrade. While many biological products may degrade by adsorbing to various surfaces, the interaction between a resin and biological product is of a different nature as evidenced by the use of resins in the purification of biological products whereby high degree of stability is maintained when eluting from a resin column.

In a biological system, a particular biological product is expressed only in a specific subcellular location, tissue or cell type, during a defined time period, and at a particular quantity level. This is the spatial, temporal, and quantitative expression. Recombinant biological product expression often introduces a foreign biological product in a host cell and expresses the biological product at levels significantly higher than the physiological level of the biological product in its native host and at the time the biological product is not needed. The over-expressed recombinant biological product will perform certain function in the host cell if the biological product is expressed soluble and functional. The function of the expressed recombinant biological product is often not needed by the host cell. In fact the function of the biological product may be detrimental to the proliferation and differentiation of the host cell. The observed phenotypes of the host cells are slow growth rate and low cell density. In some cases, the recombinant biological product causes death of the host cell. These phenomena are described as biological product toxicity. These recombinant biological products are called toxic biological products.

Biological product toxicity is a commonly observed phenomenon. All active biological products will perform certain functions. The host cells need all of these functions with few exceptions and therefore they interfere with cellular proliferation and differentiation. The appeared phenotype of the effects of these biological products to the host cells is their "toxicity". It is estimated that about 80% of all soluble biological products have certain degree of toxicity to their hosts. About 10% of all biological products are highly toxic to host cells. The completely insoluble or dysfunctional biological products will not be toxic to the host cell, though they may drain the cellular energy to produce them when over-expressed. Biological product over-expression creates metabolic burden for the host cell, but this burden is not toxicity to the cell. Some low solubility or partially functional biological products may still be toxic to the host. While the exposure of the host cell to biological product being expressed is inevitable and is only optimized through codon usage, once the biological product has been expressed, it will be prudent to transport it out of the cell as soon as possible and this diffusion reaction requires establishing a sink condition that is readily achieved if the expressed biological product in the surroundings of the host cell is removed from the solution such as in the case of the present invention by binding to a resin.

Another most significant advantage of the methods disclosed here comes in reducing the toxicity of the biological products to the biological culture expressing them; one may place the resin inside the upper chamber from the very beginning of the reaction process and as biological product is expressed, it is instantly captured by the resin removing it from direct contact with the biological culture increasing their productivity and the longevity of expression cycle, decreasing the production costs substantially. It is noteworthy that any resin adding during the process of bioreaction must be appropriately sterilized. One way to achieve this would be to introduce the resin inside the bag prior to performing sterilization of the bag using gamma radiation. While this may seem like a cumbersome procedure, this is no different than using proprietary bags for the production of proteins; once a manufacturing process is fully validated, flexible bags containing these resins can become a routine design of the bag.

In another situation, where a perfusion system is used for the upstream production of recombinant biological products, a portion of culture media is replaced with fresh media and the media removed is filtered of host cells, reduced in volume and either stored at a lower temperature or processed with downstream processing. Still another most significant advantage of the method disclosed here comes in performing a perfusion bioreaction. The traditional process of perfusion can be replaced by removing the biological product from the solution by adding a resin to the upper chamber and replenishing any nutrients that may have been lost due to adsorption onto the resin. There is a substantial cost reduction in using this substitute method.

It is noteworthy that the present invention allows for provisions to keep the bioreaction going at its optimal conditions by replenishing any nutrients lost to the binding resin; this may happen when the resins used have a non-specific binding characteristics. Where highly specific affinity binding resins are used, this step may be obviated or reduced in its frequency.

And yet another advantage of the disclosed method is that the final resin-biological product conjugate can be loaded directly column and eluted accordingly to specified protocols without first flushing it out with a buffer to break the bonding between the resin and the biological product. This will save substantial time and material savings.

A remarkable application of the present invention is made in the manufacturing of recombinant biological products using bacterial culture. E. Coli has been most widely used for the production of recombinant proteins that do not require posttranslational modifications such as glycosylation for bioactivity. A typical process involves, harvesting bacteria by a process of centrifugation, to collect the cell paste. Since the high-level expression of recombinant proteins results in accumulation of protein as insoluble aggregates as inclusion bodies, the cells are lysed, most commonly by a sonication process and the inclusion bodies solubilized (by the use of a high concentration of denaturants such as urea or guanidine hydrochloride, along with reducing agents such as beta-mercaptoethanol), refolded (by slow removal of the denaturant in the presence of oxidizing agent) and purified to recover functionality of the active product. Protein solubilization from the inclusion body using high concentration of chaotropic reagents results in the loss of secondary structure leading to the random coil formation of the protein structure and exposure of hydrophobic surface, a feature that is of significant importance in the present invention.

One embodiment of the present invention combines several procedures of cell lysis, solubilization and refolding into one continuous operation that can all be completed within the bioreactor, obviating the need for multiple containers, handing large volumes of liquids and reducing process time and cost of manufacturing.

Protein production in *Escherichia coli* involves high-level expression in a culture, followed by harvesting of the cells and finally their disruption, or lysis, to release the expressed proteins. One of the most crucial steps to be optimized in the protein production process is bacterial cell lysis. Although bacterial cell lysis does not influence protein expression, it can have an effect on protein solubility by affecting the physicochemical properties of the protein. Chemical lysis can be achieved by using different buffer composition, lysozyme, or commercially available detergent reagents. Cell lysis can also include a combination of the mechanical and chemical lysis, e.g., lysozyme with freeze-thaw cycles. The preferred method, or "gold standard", for bacterial lysis on the small or standard laboratory scale production is sonication. It relies on the mechanical disruption of the bacterial cell wall. Any solubilizing lysis agents, like detergents, that can affect solubility or stability, do not affect the expressed protein. Sonication becomes more problematic when handling large volumes of culture media. For these reasons, many high throughput laboratories choose to optimize lysis conditions by chemical means.

Chemical lysis includes the treatment of cells with alkali, enzyme, or detergents. Chemical lysis methods minimize denaturation and expose the inner, cytoplasmic membrane by degrading the peptidoglycan cell wall of bacteria. The cell wall of Gram-positive bacteria is thick, containing several interconnecting layers of peptidoglycan (60-90% of the cell was). In contrast the cell wall of Gram-negative bacteria appears thin, containing two or three layers of peptidoglycan (10-20%) of the cell wall). In addition to this, Gram-negative bacteria contain an outer membrane composed of lipopolysaccharide, phospholipids, and lipoprotein. Lysozyme, a commercial lytic enzyme, is widely used to lyse Gram-positive cells in the presence of EDTA and detergent Brij 58. Lysozyme hydrolyzes N-acetylmuramide linkages, resulting in degradation of bacterial cell walls. The activity of lysozyme is optimal in the pH range of 6.7 to 8.6.

In contrast, gram-negative bacteria are less susceptible to lysozyme and detergents due to the presence of asymmetric lipid bilayer. The outer membrane of the peptidoglycan acts as a permeability barrier to large molecules, and so the outer membrane needs to be permeabilized to expose the peptidoglycan layer for successful enzymatic lysis. The permeability barrier is, in part, due to the presence of polyanionic lipopolysaccharide that provide a network interaction in the presence of divalent cations, such as $Mg^{2+}$. The chelators of divalent carions (e.g., EDTA), polycationic species, and small molecules (e.g., Tris) are suitable for permeabilizing the membrane in order to release lipopolysachccharides.

Chemical cell lysis can be performed using lysis solution containing either lysozyme (Sigma-Aldrich, St. Louis, Mo.), SoluLyse® in Tris buffer (Genlantis, San Diego, Calif.) or Bugbuster® protein extraction reagent (Novagen, EMD Chemicals Inc., San Diego, Calif.). The amount of soluble protein and the percentage recovered in the soluble fraction using SoluLyse® well correlates with sonication. Compositions and protocols for chemical lysis are widely available through commercial suppliers of chemical lysis products. The quantity of various chemicals used, the time of exposure and determination of the end point are readily established for any specific process.

Solubilizing the lysed cell product will yield a denatured protein with large hydrophobic and ionic surfaces that can be readily bound to resins like cationic, anionic or hydrophobic resins; in some instances, certain solution characteristics like the pH, ionic strength of polarity may have to be adjusted to achieve optimal binding to the resin introduced in the upper chamber. This will allow discarding of the large volume of nutrient medium nutrient medium and cell debris; it is noteworthy that the pore size of the septum will generally be small enough to exclude cell lysis debris to contact the resin.

The solubilized proteins bound to resins can then be removed from the binding and a solution of protein allowed to refold inside the bioreactor and again once the refolding has been completed, binding the proteins to resin and discarding the refolding solution obviating the need for expensive and time consuming cross-flow filtration operations. The concentrated solutions of refolded proteins can then be subjected to further purification, if necessary.

There remains a large unmet need to develop a technology wherein the target biological product is selectively or non-selectively removed from the culture media prior to subjecting it to customary purification processes. The present invention, taking a contrarian approach, is targeted to modify the existing designs of bioreactors to include a step of performing biological product harvesting or biological product capturing prior to purification chromatography steps to increase the throughput of manufacturing processing without adding expensive and technically challenging modifications.

The key component of the present invention lies in a feature added to a traditional bioreactor, whether a hard-walled system or a flexible disposable system. A lower chamber 12 is provided in the bioreactor that serves two purposes, one is the hold gas under higher enough pressure so that it comes out of the septum 13 which has fine pores to provide the function of gasification; the same chamber 12 can also hold a resin that will bind the drug either at the end of the upstream cycle or during the upstream cycle. The pore size of the septum 13 is smaller smaller than the size of resin used to capture biological products. Most resins come in sizes ranging from 50 microns and up; some have smaller particle size as well. However, it is possible to design a septum from the same material as the flexible bag and presize the resin by holding it in a bag made of the same material and pore size and submerging the bag in water to allow the smaller size particles to be separated; the properly size resin is then used in the present invention. It is noteworthy that the resins, though expensive, can be re-used numerous times without losing their efficacy of binding and even when they do, the method descried here allows for adjusting the quantity of resin to achieve maximum capture of biological products.

A significant advancement in the art of biological product capture is provided here by disclosing that a mixture of resins can be used to obviate the binding of sites on the resin by other functional groups found in the culture media. The ultimate goal is to design a mixture of resins that will always capture the all of the biological products in the nutrient medium within the shortest period of time. Once used, the resins can be cleansed, sanitized and readied for the next use. It is important to know that there is no need for sterilizing these resins as long as they are treated chemically to reduce the microbial load.

Recent advances in the sensors available for bioreactors now make it possible to monitor many properties including dissolved oxygen, dissolved carbon dioxide, electrolyte concentration, pH, turbidity, cell count, temperature, and also the concentration of dissolved biological products, all by using non-invasive methods. The present invention can be automated by installing such sensors and more particularly a sensor to determine concentration of the biological product so that the resin can be added to the upper chamber at a certain time when the concentration of the biological product in culture media has reached a pre-determined high level and allowing it to equilibrate until such time that the concentration in the culture media decreases to a certain pre-determined low level, most likely below 1% of the highest level prior to the treatment with resin.

While the above discussion pertained mainly to a design of a bioreactor that can perform a multiplicity of functions, the container used for the process of bioreaction can have many other uses that will increase the utility of the invention not only in the field of biological product manufacturing but also in many other fields of science, technology and manufacturing.

One of the applications of the above invention is the use of the reactor to prepare a nutrient medium; the container 4 of FIG. 1 is used by adding a powdered mixture of the components of the nutrient medium through the inlet 1 and an appropriate quantity of purified water added to the upper chamber 14 through inlet 1. Allowing a gas to enter the container through inlet 9 would allow the mixture of water and the nutrient medium powder mixture to dissolve quickly. In this case, the container 4 acts as a mixing chamber. This application can now be extended to hundreds and thousands of similar processes used in other industries, from chemical to agricultural to metallurgy. This would be particularly suitable for making a solution or a suspension of a chemical that can be hazardous wherein there remains no need to clean the container, as it can be discarded. A multitude of applications are possible in the field of biodefense and those requiring preparation of hazardous materials.

The application of the present invention as mixing vessel described above can be extended to additional uses; for example, if the inlets and outlets in the upper chamber of the container are blocked or sealed and air is introduced in the container, this will cause a rise in the pressure in the container that will force any liquid in the container through the outlet port 11 when the stopcock 10 is opened. In this mode of operation, the container can be used as a pressure vessel to transfer the liquid in the container to other containers or equipment for processing. A well known example of this application will be to use it as a pressure vessel in the manufacture of sterile drugs wherein a pressure vessel is used to transfer the drug solution to the filling machine. All operations of making a drug solution can be completed in the container and then the solution transferred to a filling machine and where necessary, a filter can be installed between the pressure container and the filling machine to sterilize the solution as well. Thus the present invention is a disposable pressure vessel with multitude of uses in many industries.

Since the invention is capable of providing a pressurized environment, a base (the septum) to hold a resin, it is most ideally suited as a preparatory chromatography column. To operate the present invention as a chromatography column, a resin is first introduced in the container in the upper chamber using the liquid inlet, followed by addition of a solution of product to be purified, such as a concentrated solution of a recombinant protein. Starting the flow of gas allows mixing of the resin with the protein solution causing the protein to bind to resin; when a sufficient degree of binding is achieved, the liquid outlet is allowed to flow out through the outlet in the lower chamber, which can be opened to a predetermined size achieve a desired flow rate. The elution of specific proteins is then made by altering the pH or the polarity of the solution in the container by continuously adding chemicals that alter these properties causing a differential elution of the adsorbed proteins on the resin. Where necessary, the inlets and the outlets in the upper chamber can be closed to apply pressure for the flow of liquid outside the container.

Common Embodiments

In a first embodiment, the present invention proposes a mixing vessel capable of mixing and dissolving solutes into solvents without using any mechanism device to stir the liquid in the container.

In a second embodiment, the present invention proposes a pressure vessel capable of transferring liquid across a reasonable distance without using any external mechanical devices.

In a third embodiment, the present invention proposes a pressure vessel capable of sterilizing and transferring liquids across a reasonable distance when a filter is attached to the liquid outlet of the container. No use of external mechanical devices is required to perform this function.

In a third embodiment, the present invention proposes a bioreactor capable of growing all types of cells and organisms regardless of the gasification requirement without applying any external motion to the container and without attaching any mechanical devices to the container, either inside or outside of the bag.

In a fourth embodiment, the present invention proposes an additional function of a bioreactor of the third embodiment above by providing a ready means of harvesting of biological products in a bioreactor by capturing the biological product by binding it to a resin. No mechanical devices are required. Thus the present invention combines at least one significant step in the biological manufacturing of drugs with the upstream processing.

In a fifth embodiment, the present invention proposes a method of separating the biological product form the nutrient medium and the biological culture within the bioreactor eliminating the need for the centrifugation of the nutrient medium to remove the biological culture and filtration of the nutrient medium to reduce its volume.

In a sixth embodiment, the present invention proposes a method of purifying a biological product in a bioreactor wherein selectively binding the biological product to a resin and the eluting it gradually performs the same function that is normally performed in chromatography column. Thus, in such instance, the present invention acts like a chromatography column.

In a seventh embodiment, the present invention obviates the need for costly cross-flow filtration processes used in every type of manufacturing of biological products as in almost all instances a concentration step is involved to reduce the volume of nutrient medium that is loaded onto purification column. The purification of biological therapeutics generally involves the use of cross flow filtration (tangential flow filtration), normal flow filtration (dead ended filtration) combined with chromatographic separations. Cross flow filtration and normal flow filtration retain matter through size exclusion and are complementary to chromatography's selectivity. For processes where volumes are large such as into thousands of liters, the cost of equipment for filtration is into hundreds of thousands of dollars with expensive filters all adding to a cost that represents a major fraction of the total cost of manufacturing of recombinant drugs.

In an eighth embodiment, the present invention provides a means of continuously removing expressed biological product from a culture media to enhance the level of expression that may be depressed because of the higher concentration of biological product in the mixture. The present invention allows maintenance of a sink condition for the concentration of the biological product at all times.

In a ninth embodiment, the present invention provides a means of continuously removing expressed biological product from a culture media to reduce the toxicity of the expressed biological product to host cells and thus prolonging the cycles of expression substantially increasing the yields of production.

In a tenth embodiment, the present invention provides a means of increasing the chemical stability of expressed biological product by binding it to a resin as soon as it is expressed as the chemicals are always less stable in a solution form than in a solid form or in this case a complex form; this will substantially improve the yield of production.

In an eleventh embodiment, the present invention provides a means of substantially reducing the cost of recombinant drug manufacturing by eliminating some of the most costly and time consuming steps. The cost of using a non-specific resin is minimal as this can be used repeatedly unlike the resin used in the downstream purification where it must be replaced periodically as it loses its power to resolve the separation. Until the resin breaks down or is physically damaged, it can be used continuously and even when the efficiency of adsorption is reduced, it can be mixed with fresh resin to give it a very long useful life.

In a twelfth embodiment, the present invention combines several steps of upstream and downstream bioprocessing; in the harvesting process, the resin-biological product complex can be directly treated with buffers to begin the first stage of purification and where the resin is carefully and artfully selected, lead to high purity of a biological product in one step. The resin-biological product complex is ready for downstream processing without the need to load a column intended for downstream processing and this can save substantial time for loading; the prolonged delay in loading columns as currently practiced is often detrimental to the stability of target biological product; this can be avoided using the present invention.

In a thirteenth embodiment, the present invention provides a method of extraction of solubilized inclusion bodies by lysing the cells in the bioreactor, solubilizing the inclusion bodies and capturing them with a resin to remove them from the bioreactor. This application substantially reduces the cost of manufacturing of proteins, which are expressed as inclusion bodies.

In a fourteenth embodiment, the present invention provides a method of gasification of a nutrient medium contained in a bioreactor by providing a septum that is made of a septum installed inside the container thereby providing even distribution of gases throughout the container and help achieve a fast equilibration of gases with the nutrient medium.

In a fifteenth embodiment, the present invention provides a method of mixing the contents of nutrient medium in a bioreactor by the movement of gas inside the container and thereby eliminating all need for any mechanical means, either inside or outside the container; this element of invention introduces for the first time, a bioreactor that is totally self contained, requires no mechanical means of agitation and gasification. Both of these functions are provided by one source of gas.

In a sixteenth embodiment, a further application is provided to bioreaction systems wherein the biological product is expressed inside the cell as an inclusion body. The bioreactor is operated as described above but instead of monitoring the concentration of biological product, the optical density of the biological culture is monitored. When a predetermined optical density is reached, the bioreaction process is stopped, the cells lysed chemically and the resultant inclusion bodies solubilized, all inside the bioreactor. Once a suitable solubilization of the inclusion body has been achieved, an appropriate mixture of resins is added to bind the solubilized inclusion bodies. The rest of the method is then followed for the separation of the nutrient medium, detachment of solubilized inclusion bodies from the resin and further purification. It is further noted that there may not be a need for further filtration to remove cells, as they will all have been lysed. In some instances, the protein can be refolded within the bioreactor using appropriate refolding buffer after detaching the solubilized inclusion bodies from the resin. The bioreactor container offers a remarkable opportunity to extend the use to refold proteins eliminating the need for operating another container. It is almost ironic that in general practice, the volume of the refolding solution is generally equal to the nutrient medium, making the bioreactor and ideal choice for protein refolding.

In a seventeenth embodiment, a further utility of the present invention is provided wherein the operation of bioreactor as described above produces a mixture of the biological product and the resin and this complex can be directly loaded into chromatography purification columns avoiding another cumbersome and time-consuming step.

The above-preferred embodiments of a bioreactor design will be useful in the manufacture of all types of biological products using all types of cells and organisms. The bioreactor is operated by first adding a fixed volume of a nutrient medium to the flexible bag, which will generally be supplied, pre-sterilized by gamma radiation. The nutrient medium may be sterile filtered directly into the bag for convenience. The bag will rest on a supportive surface. The heating element is operated to heat the contents of the container to achieve a desire temperature inside the container. Sensors may be attached to the bag to record the temperature and connect these sensors to a feedback heating mechanism that will assure maintenance of an appropriate temperature such as 37° C. These sensors are not shown in FIG. 1 as they are customary and generically available. Alternately, a sample of nutrient medium may be drawn to measure its characteristics. Once the temperature reaches the desired level, a biological culture of a recombinant organism such as Chinese Hamster Ovary cell or E. Coli will be added to the nutrient medium through the nutrient medium inlet and the bag allowed mixing. Alternately, the biological culture may be added at any time, even before adding the nutrient medium. The gas is turned on to begin sparging of the nutrient medium at a rate predetermined to be suitable for the specific process. For an E. Coli expression experiment, the flow rate will be approximately 1-6 vvm of compressed gas. The key to achieving best aeration and the highest KLA value is to allow the bag to inflate only slightly, to allow sufficient surface for the sparged gas to escape, yet not cause pressurization of the bag. It is for this reason that the gas outlet is carefully controlled for the outlet rate. Once a steady state of flow rate, bag pressurization and mixing dynamics is achieved, the bioreactor is allowed to run, such as overnight when using for bacterial fermentation or for several days when using Chinese Hamster Ovary cells. During this period, the nutrient medium may be fed with nutrients through the media inlet. The optical density of bacterial culture or the cell density, dissolved oxygen and pH can be carefully monitored to assure the optimal condition for the expression of biological products in the nutrient medium. While the preferred embodiment will function only when the biological product is present in a solution form in nutrient medium, the biological processes that produce an inclusion body can also benefit from the present invention if the cells are chemically lysed and the inclusion bodies solubilized. It is now well established in prior art that solubilized inclusion bodies can be loaded onto resin columns to perform refolding of proteins and thus there exist a large number of resins that will quickly and efficiently bind solubilized inclusion bodies. Thus the present invention is applicable to bacterial production even if they do not directly express soluble proteins. However, the process of manufacture of the biological products will involve a chemical treatment to lyse the cells and then chemically solubilize the inclusion bodies prior to moving to the resin-binding step.

The next step is to calculate the amount of resin needed to bind the biological product based on the concentration of the biological product in the nutrient medium. The resin is first prepared by removing resin particles that will be smaller than the pore size of the septum (which will generally be about 20-50μ). The sized resin is then introduced directly into the upper chamber through the bottom inlet and the nutrient medium allowed to agitate by the action of gas exiting the septum. [It is expected that more than 99.9% of all resins used will have particle size larger than 50μ and thus no bleeding of resin will take place back into bioreactor}. Samples of nutrient medium are taken periodically to ascertain when the majority of the biological product has become bound to the resin inside the upper chamber. Generally, this will be above 90% reduction in the concentration of the biological product in the nutrient medium. It may be necessary to add more resin if the concentration of the biological product does not reach a pre-determined low level within a pre-determined time. The time needed for such equilibration will be about 20-30 minutes; however, specific binding rate studies will need to be conducted to assure that an optimal minimal time is allowed for such equilibration.

Once it is determined that an optimal binding of the biological product has been achieved, the drain port is operated by opening the stopcock and the culture media along with cells or organisms is allowed to flow out under gravity force. The utilization of gravity flow is a major energy and time saving feature. In those instances where thousands of liters of nutrient media is used, any mechanical process for moving or handling nutrient media will be an inefficient process compared to gravity flow resulting in discarding of nutrient media. It is further emphasized that the NIH guidelines for LSGP (large scale good practice) allow many recombinant cells to be directly discarded into sewer without any treatment as they are not infectious; this is particularly true of the Chinese Hamster Ovary Cells that comprise the largest production engine in bioprocessing. Even some E. Coli bacteria are exempted from any decontamination step. In such situations, the most energy and cost efficient process is draining of nutrient media directly into sewer. The size of the drain will have to match with the flow rate desired and where large volumes are used, several drains can be installed in the bioreactor to quickly and efficiently remove nutrient medium. Once the nutrient medium has been drained out, the stopcock in the drain is closed. At this stage, the manufacturer will have two options, one is to fill the bag with a buffer that will not cause the breaking of the binding between the biological product and the resin but will be generally effective in removing other smaller molecular weight components that might have become attached to the resin. The bag will then be agitated for a brief period of time and the buffer (which may even be water) drained out again by turning on the stopcock in the drain port. This will be the washing step. This step can be skipped and the bag filled with a buffer solution that will cause the breakdown of the binding between the biological product and the resin; this will generally require a pH adjustment, a polarity adjustment and an electrolyte adjustment. These conditions will have already been worked out in the early phases of process development. Once the breaking or eluting buffer is allowed to react within the bag, the biological product will be released into the buffer solution, which can be monitored for the concentration of the biological product to assure that a desirable recovery has been achieved. While the goal is to recover almost the entire biological product, it may at times be more useful to settle with a more practical level of recovery such as 90 to 95%. Once this stage has reached, turning on the stopcock again opens the drain port and the concentrated solution of the biological product is collected in a microbiologically clean container. Generally, the volume of the solution will be about 2-5% of the original nutrient medium. This concentrated solution will then be transferred to downstream purification columns. In most instances, it may be desirable to pass this concentrated solution through a sterilizing filter to remove any cells that might have been carried over to prevent the blocking of the purification columns. It is expected that the titer of cells at this stage will be very small allowing use of simpler and faster filtration methods and even if the solution is not filtered, the chance of blocking the purification column will be minimal. Smart manufacturing processes have the fewest steps involved; the manufacturers will be advised to consider eliminating this filtration step if possible.

The overall impact of the above embodiments is quantifiable in terms of the time it takes to make a biological product ready for purification; as a general guideline, if a 2000 L batch of a recombinant production is ready for processing, it will take about 10-12 hours to filter it through a 0.22 μmicron filter to remove host cells such as Chinese Hamster Ovary Cells; this step will then be followed by a cross-flow filtration process that might take 12-24 hours to reduce the volume to 200-300 liters; this step is then followed by loading on the column, which may take another 6-24 hours depending on the size of the column used. While the batch is subjected to above processes, the target biological product is under going degradation, both because of the effects of temperature as well as the strain exerted on biological products in the filtration process. The present invention offers a solution to replace all of these steps with a single short step with a time savings of at least 50% in the overall process time and material savings of about 30% and improved yields of about 20%.

The use of the present invention contemplates the use of pre-validated (and, preferably, pre-sterilized) containers, allowing one to provide for the production of biological products without the need for re-validation of the bioreactor.

One of the advantages of the inventive bioreactor and related method is the increase in product yield per container volume that may be obtained relative to known systems. Contributing to this increase in yield is the capability of the bioreactor to operate when the amount of nutrient medium in each container exceeds 50 vol. %, based on the interior volume of the containers. Desirably, the amount of nutrient medium in each container during operation of the bioreactor may exceed about 60 vol. % of the interior volume of the container, more desirably it may exceed about 70 vol. %, even more desirably it may exceed about 80 vol. %, it may preferably exceed about 85 vol. %, and more preferably it may exceed about 90 vol. % thereof. This increase in nutrient medium volume on a percentage basis not only provides relatively high yields per volume, but may be achieved even if the nutrient medium initially introduced into the bioreactor, or as present in the bioreactor during and/or after processing, contains relatively low levels of anti-foaming agents such as Antifoam 2210 or Compound A (Dow Corning), M-10 (Calgene), Breox FMT 30 International Specialty Company), or A6582, A6457, A6707, A8082 and A8582 (Sigma Aldrich) (from about 0.001 wt. % to about 0.005 wt. %). More desirably, the nutrient medium initially introduced into the bioreactor, or as present in the bioreactor during and/or after processing, is substantially free of such anti-foaming agents (from about 0.0001 wt. % to about 0.001 wt. %, or less than about 0.001 wt %).

Each container is provided with a gas outlet which may also include a pressure valve and submicron filter, the former assisting in maintaining the pressure within the container at a desired range while the latter assists in maintaining sterility of the nutrient medium. Desirably, the pressure in the container is maintained at ambient conditions, preferably ranging from about to about 0.1 to 1 psig. The filter may be of any suitable size and porosity, but is preferably a HEPA filter, having an average porosity of from about 0.3 μm to about 0.1 μm, and more preferably of about 0.22 μm. Gas entering the container through a gas inlet also are desirably subjected to filtration by such filter element.

It is further desirable that the container be located within a climate-controlled environment. More desirably, the containers reside within a chamber which permits independent control of one or more of the temperature of the ambient gas within the enclosure, of the gas quality, and of the radiation to which the containers are exposed. Preferably, the environment permits the independent control of the ambient temperature, gas quality and radiation for each container.

Generally, the present invention provides bioreactors and methods which are universal in the sense that the invention is suitable and adaptable for processing a variety of compositions, including both biologic and non-biologic components. Indeed, an inventive bioreactor designed for use with mammalian cells, for example, may be used for culturing bacteria, allowing ease of manufacturing.

As used herein, the term "nutrient medium" is intended to encompass compositions which include biologic components as described herein.

Compositions comprising non-biologic components include, but are not limited to, those which comprise microcarriers (e.g., polymer spheres, solid spheres, gelatinous particles, microbeads, and microdisks that can be porous or non-porous), cross-linked beads (e.g., dextran) charged with specific chemical groups (e.g., tertiary amine groups), 2D microcarriers including cells trapped in nonporous polymer fibers, 3D carriers (e.g., carrier fibers, hollow fibers, multi-cartridge reactors, and semi-permeable membranes that can comprising porous fibers), microcarriers having reduced ion exchange capacity, cells, capillaries, and aggregates (e.g., aggregates of cells).

The biological components that may be processed in accordance with the invention are described in the paragraphs which follow and include, but are not limited to, cell cultures derived from sources such as animals (e.g., hamsters, mice, pigs, rabbits, dogs, fish, shrimp, nematodes, and humans), insects (e.g., moths and butterflies), plants (e.g., algae, corn, tomato, rice, wheat, barley, alfalfa, sugarcane, soybean, potato, lettuce, lupine, tobacco, rapeseed (canola), sunflower, turnip, beet cane molasses, seeds, safflower, and peanuts), bacteria, fungi, and yeast.

Illustrative animal cells include Chinese hamster ovary (CHO), mouse myeloma, M0035 (NSO cell line), hybridomas (e.g., B-lymphocyte cells fused with myeloma tumor cells), baby hamster kidney (BHK), monkey COS, African green monkey kidney epithelial (VERO), mouse embryo fibroblasts (NIH-3T3), mouse connective tissue fibroblasts (L929), bovine aorta endothelial (BAE-1), mouse myeloma lymphoblastoid-like (NSO), mouse B-cell lymphoma lymphoblastoid (WEHI 231), mouse lymphoma lymphoblastoid (YAC 1), mouse fibroblast (LS), hepatic mouse (e.g., MC/9, NCTC clone 1469), and hepatic rat cells (e.g., ARL-6, BRL3A, H4S, Phi 1 (from Fu5 cells)).

Illustrative human cells include retinal cells (PER-C6), embryonic kidney cells (HEK-293), lung fibroblasts (MRC-5), cervix epithelial cells (HELA), diploid fibroblasts (WI38), kidney epithelial cells (HEK 293), liver epithelial cells (HEPG2), lymphoma lymphoblastoid cells (Namalwa), leukemia lymphoblastoid-like cells (HL60), myeloma lymphoblastoid cells (U 266B1), neuroblastoma neuroblasts (SH-SY5Y), diploid cell strain cells (e.g., propagation of poliomyelitis virus), pancreatic islet cells, embryonic stem cells (hES), human mesenchymal stem cells (MSCs, which can be differentiated to osteogenic, chondrogenic, tenogenic, myogenic, adipogenic, and marrow stromal lineages, for example), human neural stem cells (NSC), human histiocytic lymphoma lymphoblastoid cells (U937), and human hepatic cells such as WRL68 (from embryo cells), PLC/PRF/5 (i.e., containing hepatitis B sequences), Hep3B (i.e., producing plasma proteins: fibrinogen, alpha-fetoprotein, transferrin, albumin, complement C3 and/or alpha-2-macroglobulin), and HepG2 (i.e., producing plasma proteins: prothrombin, antithrombin III, alpha-fetoprotein, complement C3, and/or fibrinogen).

Cells from insects (e.g., baculovirus and *Spodoptera frugiperda* ovary (Sf21 cells produce Sf9 line)) and cells from plants or food, may also be cultured in accordance with the invention. Cells from sources such as rice (e.g., *Oryza sativa, Oryza sativa* cv Bengal callus culture, and *Oryza sativa* cv Taipei 309), soybean (e.g., *Glycine max* cv Williams 82), tomato (*Lycopersicum esculentum* cv Seokwang), and tobacco leaves (e.g., *Agrobacterium tumefaciens* including Bright Yellow 2 (BY-2), *Nicotiana tabacum* cv NT-1, *N. tabacum* cv BY-2, and *N. tabacum* cv Petite Havana SR-1) are illustrative examples.

Bacteria, fungi, or yeast may also be cultured in accordance with the invention. Illustrative bacteria include *Salmonella, Escherichia coli, Vibrio cholerae, Bacillus subtilis, Streptomyces, Pseudomonas fluorescens, Pseudomonas putida, Pseudomonas* sp, *Rhodococcus* sp, *Streptomyces* sp, and *Alcaligenes* sp. Fungal cells can be cultured from species such as *Aspergillus niger* and *Trichoderma reesei*, and yeast cells can include cells from *Hansenula polymorpha, Pichia pastoris, Saccharomyces cerevisiae, S. cerevisiae* crossed with *S. bayanus, S. cerevisiae* crossed with LAC4 and LAC1-2 genes from *K. lactis, S. cerevisiae* crossed with *Aspergillus shirousamii, Bacillus subtilis, Saccharomyces diastasicus, Schwanniomyces occidentalis, S. cerevisiae* with genes from *Pichia stipitis*, and *Schizosaccharomyces pombe*.

A variety of different products may also be produced in accordance with the invention. Illustrative products include proteins (e.g., antibodies and enzymes), vaccines, viral products, hormones, immunoregulators, metabolites, fatty acids, vitamins, drugs, antibiotics, cells, hydrodomas, and tissues. Non-limiting examples of proteins include human tissue plasminogen activators (tPA), blood coagulation factors, growth factors (e.g., cytokines, including interferons and chemokines), adhesion molecules, Bcl-2 family of proteins, polyhedrin proteins, human serum albumin, scFv antibody fragment, human erythropoietin, mouse monoclonal heavy chain 7, mouse IgG$_{2b/k}$, mouse IgG1, heavy chain mAb, Bryondin 1, human interleukin-2, human interleukin-4, ricin, human α1-antitrypsin, biscFv antibody fragment, immunoglobulins, human granulocyte, stimulating factor (hGM-CSF), hepatitis B surface antigen (HBsAg), human lysozyme, IL-12, and mAb against HBsAg. Examples of plasma proteins include fibrinogen, alpha-fetoprotein, transferrin, albumin, complement C3 and alpha-2-macroglobulin, prothrombin, antithrombin III, alpha-fetoprotein, complement C3 and fibrinogen, insulin, hepatitis B surface antigen, urate oxidase, glucagon, granulocyte-macrophage colony stimulating factor, hirudin/desirudin, angiostatin, elastase inhibitor, endostatin, epidermal growth factor analog, insulin-like growth factor-1, kallikrein inhibitor, α1-antitrypsin, tumor necrosis factor, collagen protein domains (but not whole collagen glycoproteins), proteins without metabolic byproducts, human albumin, bovine albumin, thrombomodulin, transferrin, factor VIII for hemophilia A (i.e., from CHO or BHK cells), factor VIIa (i.e., from BHK), factor IX for hemophilia B (i.e., from CHO), human-secreted alkaline phosphatase, aprotinin, histamine, leukotrienes, IgE receptors, N-acetylglucosaminyltransferase-III, and antihemophilic factor VIII.

Enzymes may be produced from a variety of sources using the invention. Non-limiting examples of such enzymes include YepACT-AMY-ACT-X24 hybrid enzyme from yeast, *Aspergillus oryzae* α-amylase, xylanases, urokinase, tissue plasminogen activator (rt-PA), bovine chymosin, glucocerebrosidase (therapeutic enzyme for Gaucher's disease, from CHO), lactase, trypsin, aprotinin, human lactoferrin, lysozyme, and oleosines.

Vaccines also may be produced using the invention. Non-limiting examples include vaccines for prostate cancer, human papilloma virus, viral influenza, trivalent hemagglutinin influenza, AIDS, HIV, malaria, anthrax, bacterial meningitis, chicken pox, cholera, diphtheria, *haemophilus influenza* type B, hepatitis A, hepatitis B, pertussis, plague, pneumococcal pneumonia, polio, rabies, human-rabies, tetanus, typhoid fever, yellow fever, veterinary-FMD, New Castle's Disease, foot and mouth disease, DNA, Venezuelan equine encephalitis virus, cancer (colon cancer) vaccines (i.e., prophylactic or therapeutic), MMR (measles, mumps, rubella), yellow fever, *Haemophilus influenzae* (Hib), DTP (diphtheria and tetanus vaccines, with pertussis subunit), vaccines linked to polysaccharides (e.g., Hib, *Neisseria meningococcus*), *Staphylococcus pneumoniae*, nicotine, multiple sclerosis, bovine spongiform encephalopathy (mad cow disease), IgG1 (phosphonate ester), IgM (neuropeptide hapten), SIgA/G (*Streptococcus mutans* adhesin), scFv-bryodin 1 immunotoxin (CD-40), IgG (HSV), LSC (HSV), Norwalk virus, human cytomegalovirus, rotavirus, respiratory syncytial virus F, insulin-dependent autoimmune mellitus diabetes, diarrhea, rhinovirus, herpes simplex virus, and personalized cancer vaccines, e.g., for lymphoma treatment (i.e., in injectable, oral, or edible forms). Recombinant subunit vaccines also may be produced, such as hepatitis B virus envelope protein, rabies virus glycoprotein, *E. coli* heat labile enterotoxin, Norwalk virus capsid protein, diabetes autoantigen, cholera toxin B subunit, cholera toxin B an dA2 subunits, rotavirus enterotoxin and enterotoxigenic *E. coli*, fimbrial antigen fusion, and porcine transmissible gastroenteritis virus glycoprotein S.

Viral products also may be produced. Non-limiting examples of viral products include sindbis, VSV, oncoma, hepatitis A, channel cat fish virus, RSV, corona virus, FMDV, rabies, polio, reo virus, measles, and mumps.

Hormones also may be produced using the invention. Non-limiting examples of hormones include growth hormone (e.g., human growth hormone (hGH) and bovine growth hormone), growth factors, beta and gamma interferon, vascular endothelial growth factor (VEGF), somatostatin, platelet-derived growth factor (PDGF), follicle stimulating hormone (FSH), luteinizing hormone, human chorionic hormone, and erythropoietin.

Immunoregulators also may be produced. Non-limiting examples of immunoregulators include interferons (e.g., beta-interferon (for multiple sclerosis), alpha-interferon, and gamma-interferon) and interleukins (such as IL-2).

Metabolites (e.g., shikonin and paclitaxel) and fatty acids (i.e., including straight-chain (e.g., adipic acid, Azelaic acid, 2-hydroxy acids), branched-chain (e.g., 10-methyl octadecanoic acid and retinoic acid), ring-including fatty acids (e.g., coronaric acid and lipoic acid), and complex fatty acids (e.g., fatty acyl-CoA)) also may be produced.

The containers useful in the various embodiments of the invention may be of any size suitable for containing a liquid. For example, the container may have a volume between 1-40 L, 40-100 L, 100-200 L, 200-300 L, 300-500 L, 500-750 L, 750-1,000 L, 1,000-2,000 L, 2,000-5,000 L, or 5,000-10,000 L. In some instances, the container has a volume greater than 1 L, or in other instances, greater than 10 L, 20 L, 40 L, 100 L, 200 L, 500 L, or 1,000 L. Volumes greater than 10,000 L are also possible, but not desirable. Preferably, the container volume will range between about 1 L and 1000 L, and more preferably between about 5 L and 500 L, and even more preferably between 5 L and 200 L.

The components of the bioreactors and other devices described herein which come into contact with the nutrient medium or products provided thereby desirably comprise biocompatible materials, more desirably biocompatible polymers, and are preferably sterilizable.

It should also be understood that many of the components described herein also are desirably flexible, e.g., the containers desirably comprise flexible biocompatible polymer containers (such as collapsible bags), with conduits which carry the fluids in and out of the container also desirably comprising such biocompatible polymers. The flexible material is further desirably one that is USP Class VI certified, e.g., silicone, polycarbonate, polyethylene, and polypropylene. Non-limiting examples of flexible materials include polymers such as polyethylene (e.g., linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. If desired, portions of the flexible container may comprise a substantially rigid material such as a rigid polymer (e.g., high density polyethylene), metal, and/or glass.

Desirably the containers comprise biocompatible materials, more desirably biocompatible polymers. When collapsible containers are selected for use, the container may be supported by or may line an inner surface of a support structure, e.g., the platform, the latter having container-retaining sidewalls. However, the invention may be practiced using non-collapsible or rigid containers or conduits.

The containers may have any thickness suitable for retaining the nutrient medium therewithin, and may be designed to have a certain resistance to puncturing during operation or while being handled. For example, the walls of a container may have a total thickness of less than or equal to 250 mils (1 mil is 25.4 micrometers), less than or equal to 200 mils, less than or equal to 100 mils, less than or equal to 70 mils (1 mil is 25.4 micrometers), less than or equal to 50 mils, less than or equal to 25 mils, less than or equal to 15 mils, or less than or equal to 10 mils. In certain embodiments, the container may include more than one layer of material that may be laminated together or otherwise attached to one another to impart certain properties to the container. For instance, one layer may be formed of a material that is substantially oxygen impermeable. Another layer may be formed of a material to impart strength to the container. Yet another layer may be included to impart chemical resistance to fluid that may be contained in the container.

It thus should be understood that a container and the septum may be formed of any suitable combinations of layers. The container (e.g., collapsible bag) may include, for example, 1 layer, greater than or equal to 2 layers, greater than or equal to 3 layers, or greater than equal to 5 layers of material(s). Each layer may have a thickness of, for example, less than or equal to 200 mils, less than or equal to 100 mils, less than or equal to 50 mils, less than or equal to 25 mils, less than or equal to 15 mils, less than or equal to 10 mils, less than or equal to 5 mils, or less than or equal to 3 mils, or combinations thereof.

In addition, the container preferably is seamless in order to improve its strength and avoid deposition of growing cells in the media.

All or portions of the container also are desirably translucent, or more desirably transparent, to allow viewing of contents inside the container. The latter is preferred when it is desirable to irradiate the nutrient medium within the container.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

PRIOR ART

The present invention is type of separative bioreactor. In the past substantial progress has been made in membrane bioreactors (MBR) that had the ability to separate the products within the bioreactors. The MBR process was introduced by the late 1960s, as soon as commercial scale ultrafiltration (UF) and microfiltration (MF) membranes were available. The original process was introduced by Dorr-Olivier Inc. and combined the use of an activated sludge bioreactor with a cross-flow membrane filtration loop. The flat sheet membranes used in this process were polymeric and featured pore sizes ranging from 0.003 to 0.01 μm. Although the idea of replacing the settling tank of the conventional activated sludge process was attractive, it was difficult to justify the use of such a process because of the high cost of membranes, low economic value of the product (tertiary effluent) and the potential rapid loss of performance due to membrane fouling. As a result, the focus was on the attainment of high fluxes, and it was therefore necessary to pump the mixed liquor suspended solids (MLSS) at high cross-flow velocity at significant energy penalty (of the order 10 kWh/m3 product) to reduce fouling. Due to the poor economics of the first generation MBRs, they only found applications in niche areas with special needs like isolated trailer parks or ski resorts for example.

The breakthrough for the MBR came in 1989 with the idea of Yamamoto and co-workers to submerge the membranes in the bioreactor. Until then, MBRs were designed with the separation device located external to the reactor (side-stream MBR) and relied on high transmembrane pressure (TMP) to maintain filtration. With the membrane directly immersed into the bioreactor, submerged MBR systems are usually preferred to sidestream configuration, especially for domestic wastewater treatment. The submerged configuration relies on coarse bubble aeration to produce mixing and limit fouling. The energy demand of the submerged system can be up to 2 orders of magnitude lower than that of the sidestream systems and submerged systems operate at a lower flux, demanding more membrane area. In submerged configurations, aeration is considered as one of the major parameter on process performances both hydraulic and biological. Aeration maintains solids in suspension, scours the membrane surface and provides oxygen to the biomass, leading to a better biodegradability and cell synthesis.

The other key steps in the recent MBR development were the acceptance of modest fluxes (25% or less of those in the first generation), and the idea to use two-phase bubbly flow to control fouling. The lower operating cost obtained with the submerged configuration along with the steady decrease in the membrane cost encouraged an exponential increase in MBR plant installations from the mid 90s. Since then, further improvements in the MBR design and operation have been introduced and incorporated into larger plants. While early MBRs were operated at solid retention times (SRT) as high as 100 days with mixed liquor suspended solids up to 30 g/L, the recent trend is to apply lower solid retention times (around 10-20 days), resulting in more manageable mixed liquor suspended solids (MLSS) levels (10-15 g/L). Thanks to these new operating conditions, the oxygen transfer and the pumping cost in the MBR have tended to decrease and overall maintenance has been simplified. There is now a range of MBR systems commercially available, most of which use submerged membranes although some external modules are available; these external systems also use two-phase flow for fouling control. Typical hydraulic retention times (HRT) range between 3 and 10 hours. In terms of membrane configurations, mainly hollow fiber and flat sheet membranes are applied for MBR applications.

Despite the more favorable energy usage of submerged membranes, there continued to be a market for the side stream configuration, particularly in industrial applications. For ease of maintenance the side stream configuration can be installed at low level in a plant building. Membrane replacement can be undertaken without specialist equipment, and intensive cleaning of individual banks can be undertaken during normal operation of the other banks and without removing the membranes modules from the installation.

As a result research continued with the side stream configuration, during which time it was found that full-scale plants could be operated with higher fluxes. This has culminated in recent years with the development of low energy systems which incorporate more sophisticated control of the operating parameters coupled with periodic back washes, which enable sustainable operation at energy usage as low as 0.3 kWh/m3 product.

Argonne scientists (www.anl.gov) recently used electrical force to transport organic acids away from the biocatalyst across an ion-exchange membrane and into a concentrate chamber, very similar to normal metabolism processes for handling acids. To provide the electricity in a cost efficient fashion, researchers turned to electrodeionization (EDI). EDI is an established commercial technology for producing high-purity water. Previously, Argonne scientists modified EDI so that it could be used for desalination of chemical and agricultural products. To accomplish this, researchers molded loose ion exchange resin beads into a porous resin wafer, enabling the capture of charge salts and acids at dilution levels with high-energy efficiency and significantly reduced waste streams compared to conventional processing. This became the basis for the Argonne's separative bioreactor. Researchers also realized that although direct enzyme immobilization on membranes provided excellent product separations, insufficient enzyme density limited the overall performance. In order to increase the density, the scientists integrated enzyme immobilization technology into the porous resin wafer and created a material that can efficiently produce and remove organic acids. As Argonne designed its separative bioreactor, researchers incorporated enzyme capture resin beads into the resin wafer. Sugars were converted by the immobilized biocatalyst to the target acids, and the product was electrically transported into a concentrate channel. This resulted in reactions occurring without buffering or neutralization. Argonne's immobilization technology also allows in-situ stripping and replacement of degraded enzymes without disassembling the system.

However, every type of membrane separative bioreactor disclosed utilized a similar principle of forcing a biological product across a membrane. The present invention differs significantly by providing a device capable of containing a resin capable of binding the target biological product, the membrane holding the resin has no specific function except to keep the resin separated form the bulk nutrient medium in the bioreactors and also to prevent larger scale organisms or cells to contact the resin. The separation function in the present invention is provided by a non-specific, non-electrically driven reaction.

The prior art on the design and operation of separative bioreactors is silent on the concept of present invention. The main references to separative bioreactors of use in biological sciences appear as U.S. patent application Ser. No. 10/9393, 642 file 19 Nov. 2004 wherein a separative bioreactor is disclosed. Accordingly, it is a separative bioreactor, comprising an anode and a cathode, a plurality of reaction chambers each having an inlet and an outlet and each including a porous solid ion exchange wafer having ion-exchange resins, each of the reaction chambers being interleaved between a cation exchange membrane and an anion exchange membrane or between either a cation or an anion exchange membrane and a bipolar exchange membrane, a plurality of product chambers each having an inlet and an outlet and separated from one of the reaction chambers by either a cation or an anion exchange membrane, recirculation mechanism for transporting material between the reaction chamber inlets and outlets and for transporting product between the product chamber inlets and outlets, and mechanism for supplying an electric potential between the anode and the cathode causing ions to be transported between chambers, whereby counterions retained or produced in each of the reaction chambers during the production of an ionizable organic product including product ions combine with oppositely charged ions to form molecules some or all of which are transported to reaction chamber inlets while product ions are transported into an adjacent product chamber to combine with oppositely charged ions to form product in a product stream exiting the product chamber outlets continuously recirculated to the product chamber inlets to increase the concentration of product in the product stream. None of the features described in this application are material to the present invention and none of the essential features of the present invention s are disclosed in this application.

The U.S. patent application Ser. No. 11/732,992 filed 5 Apr. 2007 discloses a porous solid ion exchange wafer comprising a combination of an biomolecule: capture-resin and an ion-exchange resin forming a charged capture resin containing a transition metal anion of +2 valence within said wafer. Additionally, this application claims a separative bioreactor, comprising an anode and a cathode, a plurality of reaction chambers at least some being formed from a porous solid ion exchange wafers having a combination of an biomolecule capture-resin and an ion-exchange resin forming a charged capture resin within said wafer and having a genetically tagged biomolecule immobilized on said charged capture resin, each of said porous solid ion exchange wafers having a charged capture resin therewithin being interleaved between a cation exchange membrane and an anion exchange membrane, and mechanism for supplying an electric potential between the anode and the cathode. None of these disclosures are common to the present invention and the essential features of the present invention are not recited in this application.

The U.S. Pat. No. 7,306,934 issued 11 Dec. 2007 discloses a porous solid ion exchange wafer for immobilizing biomolecules, said wafer comprising a combination of an biomolecule capture-resin containing a transition metal cation of +2 valence and an ion-exchange resin. The patent further discloses a separative bioreactor, comprising an anode and a cathode, a plurality of reaction chambers at least some being formed from a porous solid ion exchange wafers having a combination of art biomolecule capture-resin and an ion-exchange resin and having a genetically engineered tagged biomolecule immobilized on said biomolecule capture resin, each of said porous solid ion exchange wafers being interleaved between a cation exchange membrane and an anion exchange membrane, and mechanism for supplying an electric potential between the anode and the cathode. The present invention does not rely on any features disclosed in this patent, nor any features of the present invention are recited in this patent.

The U.S. Pat. No. 7,799,548 issued 21 Sep. 2011 is for a method of in situ stripping a genetically tagged biomolecule from a porous solid ion exchange wafer in a bioreactor, the wafer having a combination of a biomolecule capture-resin and an ion-exchange resin forming a charged capture resin within the wafer and having a genetically tagged biomolecule immobilized on said biomolecule capture-resin, comprising contacting the porous solid ion exchange wafer in the bioreactor with a stripping fluid at a temperature and for a time sufficient to strip at least some of the genetically tagged biomolecule therefrom. This patent additionally claims method of in situ stripping a genetically tagged biomolecule from a porous solid ion exchange wafer in a bioreactor and thereafter regenerating a genetically tagged biomolecule onto the porous solid ion exchange wafer, the wafer having a combination of a biomolecule capture-resin and an ion-exchange resin forming a charged capture resin within the wafer and having a genetically tagged biomolecule immobilized on said biomolecule capture-resin thereon, comprising contacting the porous solid ion exchange wafer in the bioreactor with a stripping fluid at a temperature and for a time sufficient to strip at least some of the genetically tagged biomolecules therefrom, and thereafter contacting the stripped porous solid ion exchange wafer in the bioreactor with an effective amount of a genetically tagged biomolecules at a temperature and for a time sufficient to immobilize genetically tagged biomolecules on the charged capture resin. The present invention does not rely on any disclosures made in this patent nor are any of the essential features of the present invention disclosed in this patent.

The U.S. Pat. No. 7,141,154 issued 28 Nov. 2006 discloses a method of continuously making an organic ester from a lower alcohol and an organic acid, comprising, introducing an organic acid or an organic salt into and/or producing an organic acid or an organic salt in an electrodeionization (EDI) stack having an anode and a cathode and a plurality of reaction chambers each formed from a porous solid ion exchange resin wafer interleaved between anion exchange membranes or an anion exchange membrane and a cation exchange membrane or an anion exchange membrane and a bipolar exchange membrane, providing mechanism for establishing an electric potential between the EDI anode and cathode, wherein at least some reaction chambers are esterification chambers and/or bioreactor chambers and/or chambers containing an organic acid or salt, whereby an organic acid or organic salt present in the EDI stack disassociates into a cation and an anion with the anion migrating into an associated esterification chamber through an anion exchange membrane if required and reacting with a lower alcohol in the esterification chamber to form an organic ester and water with at least some of the water splitting into a proton and a hydroxyl anion with at least some of the hydroxyl anion migrating to an adjacent chamber, said migration of ions being facilitated by establishing an electric potential across the EDI anode and cathode. The patent additionally discloses an apparatus for manufacturing an organic ester, comprising an electrodeionization (EDI) stack having an anode and a cathode and a plurality of reaction chambers each formed from a porous solid ion exchange resin wafer interleaved between anion exchange membranes or an anion exchange membrane and either a cation exchange membrane or a bipolar membrane, mechanism for establishing an electrical potential between said EDI anode and said cathode, at least some of said reaction chambers being esterification chambers or esterification chambers separated from an adjacent bioreactor chamber by an anion exchange membrane and/or an acid/base capture chamber, said bioreactor chambers each containing an ion exchange resin wafer capable of forming an organic acid or salt from an ionizable fluid flowing therein, said esterification chambers each containing an ion exchange resin wafer capable of forming an organic ester and water from a lower alcohol and an anion of an organic acid or salt, a source of anions supplied directly to said esterification chambers or supplied from adjacent chambers, and a supply of lower alcohol to said esterification chambers, whereby when a potential is established across said EDI anode and cathode at least some hydroxyl anions in said esterification chambers from water splitting migrate across said anion exchange membranes to adjacent chambers to drive the reaction to continuously produce an organic ester. None of the features disclosed in this patent are material to the present invention and none of the essential features of the present invention are disclosed or taught in this patent.

In summary, the prior art disclosed above teaches the use of porous solid ion exchange wafer for immobilizing biomolecules, said wafer comprising a combination of an biomolecule capture-resin containing a transition metal cation of +2 valence; it also teaches a separative bioreactor, comprising an anode and a cathode, a plurality of reaction chambers at least some being formed from a porous solid ion exchange wafers (above) having a combination of art biomolecule capture-resin and an ion-exchange resin and having a genetically engineered tagged biomolecule immobilized on said biomolecule capture resin, each of said porous solid ion exchange wafers being interleaved between a cation exchange membrane and an anion exchange membrane, and mechanism for supplying an electric potential between the anode and the cathode. The present invention is significantly different from the separative bioreactor taught above. First, the present invention does not require use of electrodes, or resins with a transition cation of +2 valence or immobilized metal ion affinity chromatography. The use of EDI (electrodeionization) and specific use of tags and limited nature of solvents to remove the captured biological products mainly enzymes makes this patent teachings distinctly different from the present invention. In addition, and most significantly, the prior art can not be used with the preferred embodiment of the present invention wherein flexible bioreactors are taught.

Moreover, the prior art requires additional hardware that adds substantial cost to the processing of manufacturing biological products while the present invention combines several processes into one without adding any new cost element. The prior art is also specific to certain types of molecules while the present invention is generic to every type of biological product.

The prior art on using gasification to produce mixing is often made in bubble bioreactors but in all those instances the bubbles push the nutrient medium up while the present invention that operates on a horizontal bioreactor creates a turbulent or laminar motion in the nutrient medium since the bubbles are extremely fine.

REFERENCES

Ahmad A, Pereira E O, Conley A J, Richman A S, Menassa R., Green biofactories: recombinant protein production in plants. Recent Pat Biotechnol. 2010 November; 4(3):242-59.

Atkinson, S., Research studies predict strong growth for MBR markets. Membrane Technology (2006) 8-10

Bazinet L., Electrodialytic phenomena and their applications in the dairy industry: a review. Crit Rev Food Sci Nutr. 2005; 45(4):307-26.

Cui, Z F, Chang, V, Fane, A G., The use of gas bubbling to enhance membrane process, J. Memb. Sci. 2211 (2003) 1-35

Drews, A, Evenblij, H, Rosenberger, S., Potential and drawbacks of microbiology-membrane interaction in membrane bioreactors, Environmental Progress 24 (4) (2005) 426-433

Ghosh A C, Bora M M, Dutta N N., Kadouri A., Developments in nutrient medium membrane separation of beta-lactam antibiotics. Adv Biochem Eng Biotechnol. 1991; 44:27-64.

Hubbuch J, Thömmes J, Kula M R., Biochemical engineering aspects of expanded bed adsorption. Biotechnol Adv. 2004 July; 22(6):433-44.

Kraume, M, Bracklow, U, Vocks, M, Drews, A., Nutrients Removal in MBRs for Municipal Wastewater Treatment. Wat. Sci. Tech. 51 (2005), 391-402

Le-Clech, P, Chen, V, Fane, A G., Fouling in membrane bioreactors used for wastewater treatment—A review. J. Memb. Sci. 284 (2006) 17-53.

Shirgaonkar I Z, Lanthier S, Kamen A., Acoustic cell filter: a proven cell retention technology for perfusion of animal cell cultures. J Gen Appl Microbiol. 2003 August; 49(4): 219-33.

Shukla A A, Thömmes J., Recent advances in large-scale production of monoclonal antibodies and related proteins. Trends Biotechnol. 2010 May; 28(5):253-61.

Singh, S M, Panda A K, Judd, S., Solubilization and refolding of bacterial inclusion body proteins. J. Biosciences and Bioengineering, 99:4, 303-310, 2005

Stephenson, T, Judd, S, Jefferson, B, Brindle, K., Membrane bioreactors for wastewater treatment, IWA Publishing (2000)

The MBR book (2006) Principles and applications of membrane bioreactors in water and wastewater treatment, Elsevier, Oxford Toda K., Theoretical and methodological studies of continuous microbial bioreactors. Biotechnol Bioeng. 2003 Jun. 30; 82(7):751-65.

Voisard D, Meuwly F, Ruffieux P A, Baer G, Potential of cell retention techniques for large-scale high-density perfusion culture of suspended mammalian cells. Bioseparation. 1996 April; 6(2):91-105.

Wu M, Wu R, Zhang Z, Zou H., Preparation and application of organic-silica hybrid monolithic capillary columns. Electrophoresis. 2011 January; 32(1):105-15.

Add functions mixing, buffer and media preparation, aeration, biological growth, harvesting and purification: talk about step elution and gradient elution with gas flow keeping the pores open; make a list of all applications as embodiments.

I claim:

1. A reactor capable of holding liquid comprising:
   a) A flexible disposable bag comprising a top layer, a bottom layer, and a perforated sparging middle layer held in close proximity to the bottom layer by a plurality of spot-welds between the bottom layer and the middle layer;
   b) At least one liquid inlet; and at least one liquid outlet;
   c) At least one gas outlet connected to the top layer
   d) At least one gas inlet connected to the bottom layer and further connected to a source of compressed gas;
   e) At least one sampling port;
   f) An outer support to hold the bag, additionally comprising a heating and/or cooling element.

2. The reactor according to claim 1, wherein the flexible disposable bag is capable of withholding a pressure of up to at least one-pound force per square inch or 6,894.76 Pascals.

3. The reactor according to claim 1, wherein the top, the bottom, and the middle layers are made of polyethylene, polypropylene, or polycarbonate.

4. The reactor according to claim 1, wherein the perforations in the middle layer are distributed uniformly or non-uniformly throughout the middle layer.

5. The reactor according to claim 1, wherein the diameter of the perforations in the middle layer ranges from about 1 µm to about 1000 µm.

6. The reactor according to claim 1, wherein the perforations in the middle layer are from about 1/32 to about 1 inch apart.

7. The reactor according to claim 1, wherein the liquid is nutrient media or buffer solution.

* * * * *